US012735504B2

(12) United States Patent
Booth et al.

(10) Patent No.: US 12,735,504 B2
(45) Date of Patent: Sep. 15, 2026

(54) ANTI D-DIMER RECOMBINANT ANTIBODIES, METHODS AND USES THEREOF

(71) Applicant: F. Hoffmann-La Roche AG, Basel (CH)

(72) Inventors: Elizabeth A. Booth, Emeryville, CA (US); Charles Holz, Emeryville, CA (US); Tristan Wasley, Emeryville, CA (US); Virginia Montanini, Sant Cugat del Valles (ES); Jody Berry, Emeryville, CA (US)

(73) Assignee: F. HOFFMANN-LA ROCHE AG, Basel (CH)

( * ) Notice: Subject to any disclaimer, the term of this patent is extended or adjusted under 35 U.S.C. 154(b) by 1050 days.

(21) Appl. No.: 17/793,483

(22) PCT Filed: Feb. 19, 2021

(86) PCT No.: PCT/IB2021/051438
§ 371 (c)(1),
(2) Date: Jul. 18, 2022

(87) PCT Pub. No.: WO2021/165914
PCT Pub. Date: Aug. 26, 2021

(65) Prior Publication Data

US 2023/0082465 A1 Mar. 16, 2023

Related U.S. Application Data

(60) Provisional application No. 62/979,253, filed on Feb. 20, 2020.

(51) Int. Cl.
*C07K 16/36* (2006.01)

(52) U.S. Cl.
CPC ........ *C07K 16/36* (2013.01); *C07K 2317/565* (2013.01); *C07K 2317/92* (2013.01); *C07K 2319/20* (2013.01)

(58) Field of Classification Search
None
See application file for complete search history.

(56) References Cited

U.S. PATENT DOCUMENTS

| | | | | |
|---|---|---|---|---|
| 6,180,370 | B1 * | 1/2001 | Queen | A61P 19/02 435/69.6 |
| 8,940,489 | B2 * | 1/2015 | Doh | C07K 16/18 435/7.1 |
| 10,112,990 | B2 | 10/2018 | Adolfsson et al. | |
| 11,159,971 | B2 | 10/2021 | AlBanna | |
| 2009/0298100 | A1 | 12/2009 | Doh et al. | |
| 2013/0011869 | A1 | 1/2013 | Nagahama et al. | |
| 2016/0047903 | A1 | 2/2016 | Dussan | |
| 2019/0224339 | A1 | 7/2019 | Paul et al. | |
| 2020/0022462 | A1 | 1/2020 | Lee et al. | |
| 2020/0339682 | A1 | 10/2020 | Kamogawa et al. | |
| 2021/0047389 | A1 | 2/2021 | Kobie et al. | |
| 2021/0070881 | A1 | 3/2021 | Dennis et al. | |
| 2022/0204582 | A1 | 6/2022 | Chaudhary | |

FOREIGN PATENT DOCUMENTS

| | | | |
|---|---|---|---|
| EP | 0348875 | A2 | 1/1990 |
| EP | 2554673 | A1 | 2/2013 |
| JP | 61222175 | A | 10/1988 |
| JP | 2018531002 | A | 10/2018 |
| KR | 20200122467 | A | 10/2020 |
| WO | 2007013709 | A1 | 2/2007 |
| WO | 2011041518 | A1 | 4/2011 |
| WO | 2011125875 | A1 | 10/2011 |
| WO | 2017050722 | A1 | 3/2017 |
| WO | 2017193096 | A1 | 11/2017 |
| WO | 2019133512 | A1 | 7/2019 |
| WO | 2019237350 | A1 | 12/2019 |
| WO | 2020113054 | A1 | 6/2020 |
| WO | 2020144697 | A1 | 7/2020 |
| WO | 2020210665 | A1 | 10/2020 |
| WO | 2020228806 | A1 | 11/2020 |
| WO | 2021032078 | A1 | 2/2021 |

OTHER PUBLICATIONS

Piche-Nicholas, Nicole M., et al. "Changes in complementarity-determining regions significantly alter IgG binding to the neonatal Fc receptor (FcRn) and pharmacokinetics." MAbs. Vol. 10. No. 1. Taylor & Francis, 2018 (Year: 2018).*
Sela-Culang, Inbal, Vered Kunik, and Yanay Ofran. "The structural basis of antibody-antigen recognition." Frontiers in immunology 4 (2013): 302 (Year: 2013).*
Janeway, Charles A. "Immunobiology: The Immune System in Health and Disease." 2001 (Year: 2001).*
Kipriyanov, Sergey M., and Fabrice Le Gall. "Generation and production of engineered antibodies." Molecular biotechnology 26.1 ( 2004): 39-60. (Year: 2004).*
Rylatt, D.B. et al. "An Immunoassay for Human D Dimer Using Monoclonal Antibodies" Pergamon Press Ltd., 1983, pp. 767-778, vol. 31.
Soe, Gilbu et al. " Analysis of Plasmin-digests of Cross-linked Fibrin Utilizing an Antibody Recognizing the Amino-Terminal Conformation of Fragment D" Japanese Journal of Thrombosis and Hemostasis, 1994, pp. 105-113, vol. 5 Issue 2.

(Continued)

*Primary Examiner* — Misook Yu
*Assistant Examiner* — Lia E Taylor
(74) *Attorney, Agent, or Firm* — Dinsmore & Shohl LLP

(57) ABSTRACT

This application relates to anti-D-Dimer recombinant antibodies that specifically bind to fibrin and fibrinogen degradation products (FDP) such as D-Dimer, fragment DD and fragment D with high binding affinity and do not bind to fragment E and fibrinogen. The present invention also refers to methods and assays for detection of D-Dimer and FDP fragments in samples using said recombinant antibodies.

12 Claims, 6 Drawing Sheets

Specification includes a Sequence Listing.

(56) References Cited

OTHER PUBLICATIONS

Holvoet, P. et al. "Binding Properties of Monoclonal Antibodies against Human Fragment of D-Dimer of Cross-Linked Fibrin to Human Plasma Clots in an In Vivo Model of Rabbits" Thrombosis and Haemostasis, 1989, pp. 307-313, vol. 61.
Torok-Nagy, Beata et al. "Generation and characterization of D-dimer specific monoclonal antibodies for use in latex agglutination test" Plos One, 2019, pp. 1-10, vol. 14.
Castillo et al., "Hybridoma stability", Dev. Biol. Stand. 83, 55-64, 1994, Abstract Only.
International Search Report pertaining to Application No. PCT/IB2021/051438 dated May 4, 2021.
Holvoet et al., "Binding Properties of Monoclonal Antibodies against Human Fragment D-Dimer of Cross-Linked Fibrin to Human Plasma Clots in an In Vivo Model in Rabbits", Thrombosis and Haemostasis, vol. 61, No. 2, pp. 307-313, 1989.
Weitz et al., "A Test in Context: D-Dimer", Journal of the Americal College of Cardiology, vol. 70, No. 19, 2017.
Adam et al., "D-dimer antigen: current concepts and future prospects", Blood, vol. 113, No. 13, pp. 2878-2887, Mar. 26, 2009.
Chothia et al., "Conformations of immunoglobulin hypervariable regions", Nature, vol. 342, pp. 877-883 , Dec. 21/28, 1989.
Coco-Martin et al., "Instability of Hybridoma Cell Line in a Homogeneous Continuous Perfusion Culture System", Hybridoma, vol. 11, No. 5, Nov. 5, 1992.
Doh et al., "Novel monoclonal antibody that recognizes new neoantigenic determinant of D-dimer", Thrombosis Research, vol. 118, pp. 353-360, 2006.
Dong et al., "Generation of a Monoclonal Antibody against D-Dimer Using HTS-Based LiCA", SLAS Disclovery, vol. 25, No. 3, pp. 310-319, 2020.
Goodacre et al., "Variation in the diagnostic performance of D-dimer for suspected deep vein thrombosis", Q J Med, vol. 98, pp. 513-527, Jun. 13, 2005.
Gupta et al., "Glycosylation control technologies for recombinant therapeutic proteins", Applied Microbiology and Biotechnology, vol. 102, p. 10457-10468, 2018.
Holvoet et al., "A Monoclonal Antibody Preventing Binding of Tissue-Type Plasminogen Activator to Fibrin: Useful to Monitor Fibrinogen Breakdown During t-PA Infusion", Blood, vol. 67, No. 5, pp. 1482-1487, May 1986.
Kogan et al., "Monoclonal antibodies with equal specificity to D-dimer and high-molecular-weight fibrin degradation products", Blood Coagulation & Fibrinolysis, vol. 27, No. 5, Dec. 11, 2015.
Lefranc et al., "IMGT, the international ImMunoGeneTics information system", Nucleic Acids Research, vol. 33, 5 ogs., 2005.
Lippi et al., "Interference from heterophilic antibodies in D-dimer assessment. A case report", Blood Coagulation and Fibrinolysis, vol. 25, No. 3, pp. 277-279, 2014.
Maccallum et al., "Antibody-antigen Interactions: Contact Analysis and Binding Site Topography", J. Mol. Bio., vol. 262, pp. 72-745, 1996.
Makabe et al., "Thermodynamic Consequences of Mutations in Vernier Zone Residues of a Humanized Anti-human Epidermal Growth Factor Receptor Murine Antibody, 528", The Journal of Biological Chemistry, vol. 283, No. 2, pp. 1156-1166, Jan. 11, 2008.
Morris et al., "Improved imaging of deep venous thrombi during anticoagulation using radiolabelled anti-D-dimer antibodies", Nuclear Medicine, vol. 25, No. 9, pp. 917-922, 2004.
Pfitzner et al., "Fabin Detected in Plasma of Patients with Disseminated Intravascular Coagulation by Fibrin-specific Antibodies Consists Primarily of High Molecular Weight Factor XIIIa-crosslinked and Plasmin-modified Complexes Partially Containing Fibrinopeptide A", Thromb Haemost, vol. 78, pp. 1069-1078, 1997.
Riley et al., "Widely Used Types and Clinical Applications of D-Dimer Assay", Laboratory Medicine, Vo91. 47, No. 2, bp. 90-102, Mar. 25, 2016.
Robier et al., "False-positive D-dimer result in a latex-enhanced immunoassay caused by interfering human antimouse antibodies", Clin Chem Lab Med, vol. 52, No. 11, pp. e253-e255, 2014.
Tasic et al., "Biosensing of D-dimer, making the transition from the central hospital laboratory to bedside determination", Talanta, vol. 207, 8 p. 2020.
Thachil et al., "D-Dimer Testing: Laboratory Aspects and Current Issues", Hemostasis and Thrombosis: Methods and Protocols, Methods in Molecular Biology, vol. 1646, pp. 91-104, 2017.
Dan, Zhaokui, et al. Construction and Expression of D-dimer and GPllb/Illa single-chain bispecific antibody, Experimental and Therapeutic Medicine May 16, 2013, 552-556, 6.
Communication pursuant to Article 94(3) EPC corresponding to European Patent Application No. 21708752.7, dated 1 Mar. 9, 2026, 11 pages, European Patent Office (EPO). .

* cited by examiner

ANTI D-DIMER RECOMBINANT ANTIBODIES, METHODS AND USES THEREOF

TECHNICAL FIELD

This application relates to anti-D-Dimer recombinant antibodies that specifically bind to fibrin and fibrinogen degradation products (FDP) such as D-Dimer, fragment DD and fragment D with high binding affinity and do not bind to fragment E and fibrinogen. The present invention also refers to methods and assays for detection of D-Dimer and FDP fragments in samples using said recombinant antibodies.

BACKGROUND

Fibrinogen is a circulating soluble protein present in blood plasma, that when treated with the enzyme thrombin (Factor IIa) forms fibrin polymers during the coagulation cascade. Fibrinogen consists of three chains; alpha, beta, and gamma, that form a larger dumbbell shaped structure with two D domains as the ends and a central E domain. Fibrin polymers are generated from the staggered assembly of fibrinogen monomers. The Fibrin polymers can be further crosslinked by Factor XIII (FXIII) forming isopeptide bonds, covalently linking the fibrin chains.

During fibrinolysis, crosslinked fibrin polymers, the product of coagulation, are degraded by the serine protease plasmin resulting in a heterogeneous mix of degradation products, the smallest of which is D-Dimer (FIG. 1). Other fibrin(ogen) degradation products (FDPs) are fragments X,Y, D and E. D-Dimer consists of two crosslinked D domains and an E domain. The D domains and the E domain can be separated by urea extraction resulting in fragment DD and E. Fragment DD is unique due to the dimerization being stabilized by the isopeptide bonds between the two D domains.

Detection of fibrin(ogen) degradation products (FDPs) is utilized in the diagnosis of venous thromboembolism (VTE) such as deep vein thrombosis (DVT) and pulmonary embolism (PE). When present in large amounts, FDPs can interfere with the hemostatic processes by binding to platelet surfaces interfering with platelet function and forming soluble complexes with fibrin monomer, preventing polymerization and clot stabilization.

D-Dimer and fragment DD are interesting for diagnostics due to the presence of the crosslinked D domains, being indicative of a coagulation incident such as a DVT or PE. There are many current D-Dimer assays available, however, they are all different due to the use of different monoclonal antibodies that recognize different epitopes, different assay formats, assay calibration standards and ranges, and different instrumentation[1]. ELISA and agglutination based assays are the most common and tests can be either qualitative or quantitative. The agglutination tests come in many formations and in the case of automated latex assays, beads conjugated with anti D-Dimer antibodies agglutinate in the presence of patient plasma and turbidimetric detection is used to characterize the agglutination. In some devices, a bispecific antibody that binds both D-Dimer and red blood cells, is used to cause red blood cell agglutination providing a qualitative result[2].

D-Dimer assays are one of the most commonly requested coagulation tests, most commonly used to rule out venous thromboembolism (VTE). VTE occurs when a blood clot forms in the deep veins of the limbs or groin (DVT) and may travel to the lungs (PE)[3]. The International Society of Thrombosis and Haemostasis has endorse the role of D-Dimer testing for disseminated intravascular coagulation (DIC). However, circulating D-Dimer can be present in coronary artery disease, cancer, trauma, pregnancy, infectious disease, inflammatory disease, advanced age, and many other conditions and disease states[4]. D-Dimer test, when utilized in the diagnostic cascade for DVT or PE, can rule out further testing for DVT or PE. This highlights the importance of having a sensitive test such that patients with VTE are not being inappropriately ruled out. In general the sensitivity of the ELISAs is higher than the latex agglutination assays, however, the value of automation and reproducibility make the latex assays more tractable in many clinical laboratories. The specificity of the D-Dimer test for a particular diagnosis is dependent on the pre-test probability[5]. Additionally, D-Dimer tests can be sensitive to interference from heterophilic antibodies[6] or sensitive to interfering human anti-mouse antibodies (if a mouse anti D-Dimer monoclonal antibody is utilized)[7]. Like most clinical tests, it cannot exist in isolation and needs to be considered as part of a larger body of evidence during the diagnostic process.

Many anti D-Dimer monoclonal antibodies have been generated and are produced as hybridomas either in supernatant or when injected into a mouse abdomen to produce ascites fluid. Although hybridomas are often a robust and efficient way to produce monoclonal antibodies (mAbs), there are limitations to the technique. First, hybridomas can become exhausted and quit producing antibodies, despite producing cell banks, it could be possible to lose the hybridoma as a production source. Second, hybridomas can be lost due to freezer failures or other accidents. And lastly, hybridomas produce antibodies in their native form, making sequencing and recombinant expression necessary for further engineering the mAbs.

Therefore, there is a need for anti D-Dimer antibodies that could be easily and reproducibly generated, and which provide high specificity for D-Dimer to be used in thrombus detection assays.

The present invention provides recombinant antibodies and antigen-binding fragments (Fab, or $F(ab')_2$) capable of specifically detecting FDPs, with several advantages over monoclonal antibodies (produced in hybridomas) of the state of the art.

First, there is increased control and reproducibility in use a recombinant protein, than one generated from a hybridoma cell line which are generally regarded as unstable[8,9]. Second, greater lot-to-lot consistency can be achieved by using stable cell lines with controlled biochemical and physical process parameters[10]. Third, animal-free technology allows for the production without using any animals eliminating welfare and ethical concerns. Fourth, the recombinant antibodies of the present invention can be engineered to comprise other functional domains for purification or solubility purposes, among others. Fifth, if required, the isotype (IgG1, IgG2a, IgG3) can be selected to generate a more highly produced or stable protein. Lastly, by being able to engineer the recombinant protein provides added advantage in decreasing the possibility of human anti-mouse antibodies interfering (HAMA)[7] which has been shown in cases-studies to cause unclear readings, adversely affecting the diagnosis of the patient.

Thus, the present invention relates to recombinant antibodies that enable assays for detection of D-Dimer, fragment DD and fragment D, having utility in the clinic in diagnosis DVT, PE, and other acute disease states.

SUMMARY

A first aspect of the present invention relates to an anti-D-dimer recombinant antibody that specifically binds to fibrin and fibrinogen degradation products (FDP) D-Dimer, fragment DD and fragment D and it does not bind to fragment E and fibrinogen.

In one embodiment, said recombinant antibody comprises a light chain comprising complementary determining regions L-CDR1, L-CDR2 and L-CDR3, each of them comprising a sequence of at least five contiguous amino acids selected from the amino acid sequence of SEQ ID NO: 18. In one preferred embodiment, said at least five contiguous amino acids selected from the amino acid sequence of SEQ ID NO: 18 include at least one of amino acids 24 to 34, or 50 to 56 or 89 to 97 of SEQ ID NO: 18. In one preferred embodiment, said L-CDR1, L-CDR2 and L-CDR3 of the light chain comprise respectively the amino acid sequence of SEQ ID NO: 31, SEQ ID NO: 32 and SEQ ID NO: 33.

In one embodiment, said light chain comprises the amino acid sequence of SEQ ID NO: 18.

In another embodiment, said recombinant antibody comprises a heavy chain comprising complementary determining regions H-CDR1, H-CDR2 and H-CDR3, each of them comprising a sequence of at least five contiguous amino acids selected from the amino acid sequence of SEQ ID NO: 19, or SEQ ID NO: 20, or SEQ ID NO: 21 or SEQ ID NO: 22. In a preferred embodiment, said at least five contiguous amino acids selected from the amino acid sequence of SEQ ID NO: 19, or SEQ ID NO: 20, or SEQ ID NO: 21 or SEQ ID NO: 22 include at least one of amino acids 31 to 35, or 50 to 65 or 95 to 102 of SEQ ID NO: 19, or of SEQ ID NO: 20, or of SEQ ID NO: 21 or of SEQ ID NO: 22. In one preferred embodiment said H-CDR1, H-CDR2 and H-CDR3 of the heavy chain comprise respectively the amino acid sequence of SEQ ID NO: 34, SEQ ID NO: 35 and SEQ ID NO: 36.

In some embodiments, the recombinant antibody of the present invention may have a heavy chain H-CDR1, H-CDR2 and H-CDR3 comprising the amino acid sequences of SEQ ID NO: 34, SEQ ID NO: 37, and SEQ ID NO: 36 respectively.

In some embodiments, the recombinant antibody of the present invention may have a heavy chain H-CDR1, H-CDR2 and H-CDR3 comprising the amino acid sequences of SEQ ID NO: 34, SEQ ID NO: 38, and SEQ ID NO: 36 respectively.

In one embodiment, said heavy chain comprises the amino acid sequence of SEQ ID NO: 19, or SEQ ID NO: 20, or SEQ ID NO: 21 or SEQ ID NO: 22.

In one embodiment, the recombinant antibody of the present invention may comprise:

- a light chain variable region comprising the amino acid sequence of SEQ ID NO: 31 (L-CDR1); the amino acid sequence of SEQ ID NO: 32 (L-CDR2); and the amino acid sequence of SEQ ID NO: 33 (L-CDR3); and
- a heavy chain variable region comprising the amino acid sequence of SEQ ID NO: 34 (H-CDR1); the amino acid sequence of SEQ ID NO: 35 (H-CDR2); and the amino acid sequence of SEQ ID NO: 36 (H-CDR3).

In another embodiment, the recombinant antibody of the present invention may comprise:

- a light chain variable region comprising an amino acid sequence at least about 85%, 90%, 91%, 92%, 93%, 94%, 95%, 96%, 97%, 98%, or about 99% identical to the sequence set forth in SEQ ID NO: 18, and
- a heavy chain variable region comprising an amino acid sequence at least about 85%, 90%, 91%, 92%, 93%, 94%, 95%, 96%, 97%, 98%, or about 99% identical to a sequence selected from the group consisting of SEQ ID NOs: 19, 20, 21, and 22.

In yet a further embodiment, the recombinant antibody of the present invention may comprise:

- a light chain variable region comprising the amino acid sequence set forth in SEQ ID NO: 18, and
- a heavy chain variable region comprising an amino acid sequence selected from the group consisting of SEQ ID NOs: 19, 20, 21, and 22.

In some embodiments the recombinant antibody of the present invention may comprise:

- a light chain variable region comprising the amino acid sequence set forth in SEQ ID NO: 18, and
- a heavy chain variable region comprising an amino acid sequence selected from the group consisting of SEQ ID NOs: 19 and 20.

In another embodiment, the recombinant antibody of the present invention is a monoclonal antibody or an antibody fragment. In some embodiments, said antibody fragment is selected from variable fragments (Fv), single-chain Fvs (scFv), bispecific antibodies ($sc(Fv)_2$), single chain antibodies, single domain antibodies, Fab fragments, $F(ab')_2$ fragments, Fab' fragments, disulfide-linked Fv (dsFv), chemically conjugated Fv (ccFv), diabodies, anti-idiotypic (anti-Id) antibodies, affibodies, nanobodies, and unibodies. In another embodiment, said antibody fragment is an antigen-binding fragment selected from a Fab fragment and a $F(ab')_2$ fragment.

In one embodiment, the recombinant antibody of the present invention comprises a constant region of the murine IgG1 class or the murine IgG2a class.

In another embodiment, the recombinant antibody of the present invention further comprises an affinity tag. Said affinity tag can be selected from the group consisting of SEQ ID NO: 23, SEQ ID NO: 24, or SEQ ID NO: 25.

In a further embodiment, the light chain of the recombinant antibody of the present invention comprises the amino acid sequence of SEQ ID NO: 17. In another embodiment, the heavy chain of the recombinant antibody of the present invention comprises the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, or SEQ ID NO:16.

In another embodiment, the light chain of the recombinant antibody of the present invention comprises the amino acid sequence of SEQ ID NO: 17 and the heavy chain of said recombinant antibody comprises the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, or SEQ ID NO:16.

In another embodiment described herein, the recombinant antibody comprises the amino acid sequence of SEQ ID NO: 17 and the amino acid sequence of SEQ ID NO: 12.

In one embodiment, the recombinant antibody of the present invention is bound to a solid support.

In another embodiment, the binding affinity of the recombinant antibody of the present invention with fragment DD is at least (about) 3 times tighter than the binding affinity of said recombinant antibody with fragment D. For example, the binding affinity of the recombinant antibody of the present invention with fragment DD is at least (about) 10 times tighter than the binding affinity of said recombinant antibody with fragment D. In another embodiment, the binding affinity of the recombinant antibody of the present invention with fragment DD is at least (about) 20 times tighter than the binding affinity of said recombinant antibody with fragment D. In another embodiment, the binding affinity of the recombinant antibody of the present invention with fragment DD is at least (about) 30 times tighter than the binding affinity of said recombinant antibody with fragment D. In another embodiment, the binding affinity of the recombinant antibody of the present invention with fragment DD is at least (about) 40 times tighter than the binding affinity of said recombinant antibody with fragment D. In another embodiment, the binding affinity of the recombinant antibody of the present invention with fragment DD is at least (about) 50 times tighter than the binding affinity of said recombinant antibody with fragment D. In another embodiment, the binding affinity of the recombinant antibody of the present invention with fragment DD is at least (about) 60 times tighter than the binding affinity of said recombinant antibody with fragment D. In another embodiment, the binding affinity of the recombinant antibody of the present invention with fragment DD is at least (about) 70 times tighter than the binding affinity of said recombinant antibody with fragment D. In another embodiment, the binding affinity of the recombinant antibody of the present invention with fragment DD is at least (about) 80 times tighter than the binding affinity of said recombinant antibody with fragment D.

In another embodiment, the binding affinity of the recombinant antibody of the present invention with fragment DD may be between at least about 20 and about 100 times tighter than the binding affinity of said recombinant antibody with fragment D. For example, the binding affinity of the recombinant antibody of the present invention with fragment DD may be between at least about 40 and about 100 times tighter than the binding affinity of said recombinant antibody with fragment D. For example, the binding affinity of the recombinant antibody of the present invention with fragment DD may be between at least about 60 and about 100 times tighter than the binding affinity of said recombinant antibody with fragment D. For example, the binding affinity of the recombinant antibody of the present invention with fragment DD may be between at least about 70 and about 100 times tighter than the binding affinity of said recombinant antibody with fragment D. For example, the binding affinity of the recombinant antibody of the present invention with fragment DD may be between at least about 70 and about 90 times tighter than the binding affinity of said recombinant antibody with fragment D. For example, the binding affinity of the recombinant antibody of the present invention with fragment DD may be between at least about 80 and about 90 times tighter than the binding affinity of said recombinant antibody with fragment D.

In another embodiment, the binding affinity of the recombinant antibody of the present invention with fragment DD is at least 1 order of magnitude tighter than the binding affinity of said recombinant antibody with fragment D. For example, the binding affinity of the recombinant antibody of the present invention with fragment DD is about 2 orders of magnitude tighter than the binding affinity of said recombinant antibody with fragment D. In one embodiment, the binding affinity of the recombinant antibody of the present invention with fragment DD is at least 1 but less than 3 orders of magnitude tighter than the binding affinity of said recombinant antibody with fragment D.

As used herein, the term "binding affinity" refers to the strength of interaction between an antigen's epitope and an antibody's antigen binding site as measured by biolayer interferometry on a an Octet Red96e system from Sartorius (previously ForteBio) at about 23° C. and 1 atm pressure.

Advantageously, compared to commercially available anti D-Dimer antibodies, the recombinant antibody/antibodies of the present invention exhibit improved binding with fibrin degradation products. Moreover, the recombinant antibody/antibodies of the present invention show no binding affinity to fibrinogen or fragment E.

In a further aspect, the present invention refers to a cell comprising the recombinant antibody of the present invention. The present invention also refers to a nucleic acid comprising a nucleotide sequence encoding the recombinant antibody of the present invention, a promoter operably linked to the nucleotide sequence and a selectable marker. The present invention also relates to a cell comprising said nucleic acid.

The present invention also refers to a composition comprising the recombinant antibody of the present invention and a solid support, wherein said recombinant antibody is covalently or non-covalently bound to the solid support. In a preferred embodiment the solid support comprises a particle, a bead, a membrane, a surface, a polypeptide chip, a microtiter plate, or the solid-phase of a chromatography column. Preferably, said solid support is a latex particle.

In another aspect, the present invention refers to a kit for detecting the presence of D-Dimer, fragment DD and/or fragment D in a sample, said kit comprising at least one recombinant antibody according to the present invention and a solid support, wherein said at least one recombinant antibody is covalently or non-covalently bound to a solid support.

In a further aspect, the present invention refers to a method for detecting the presence of D-Dimer, fragment DD and/or fragment D in a sample, said method comprising:

contacting said sample with at least one recombinant antibody of the present invention for a time and under conditions sufficient for the formation of an antibody/antigen complex, and detecting said antibody/antigen complex.

In another aspect, the present invention refers to a method of measuring the binding affinity of D-Dimer, fragment DD and/or fragment D in a sample, said method comprising:

contacting said sample with at least one recombinant antibody of the present invention for a time and under conditions sufficient for the formation of an antibody/antigen complex, and determining the binding affinity between the antibody and D-Dimer, fragment DD and/or fragment D in the sample.

In a further aspect, the present invention refers to a method of measuring the concentration of D-Dimer, fragment DD and/or fragment D in a sample, said method comprising:

contacting said sample with at least one recombinant antibody according to the present invention for a time and under conditions sufficient for the formation of an antibody/antigen complex, and measuring the concentration of D-Dimer, fragment DD and/or fragment D in the sample.

DEFINITIONS

Figure 1:
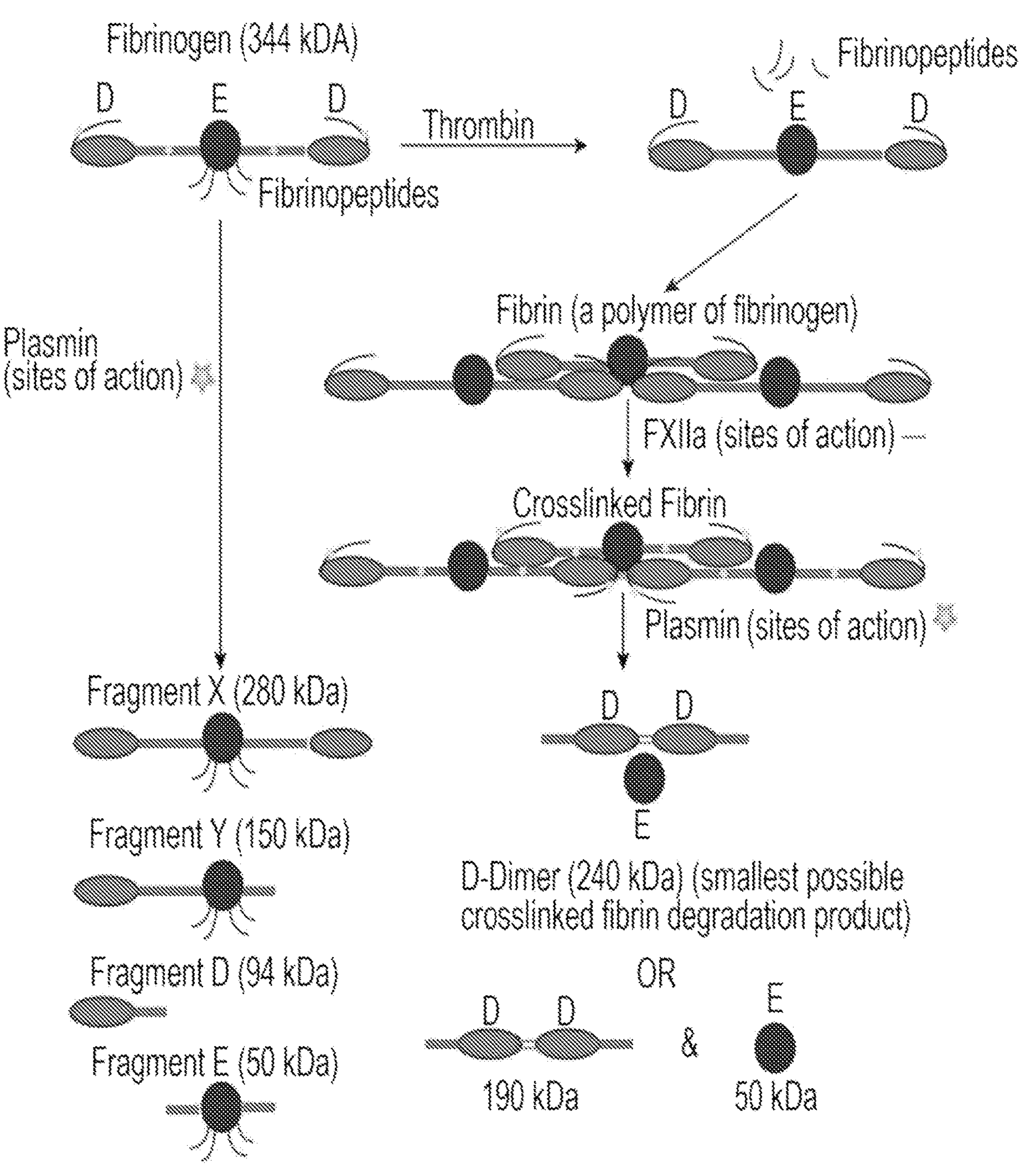
FIG. 1 is a schematic of fibrin monomers assembling to form fibrinogen. Thrombin acts on fibrin or fibrinogen to release fibrinopeptides at the E domain from the α and β chains resulting in polymerization of fibrin to fibrinogen thought staggered linking of the fibrin. FXIIIa stabilizes the protofilament by crosslinking the α-α and γ-γ chains by forming isopeptide bonds. The serine protease plasmin digests fibrin resulting in Fragments X (280 kDa), Y (150 kDa), D (94 kDa), and E (50 kDa). Due to crosslinking by FXIIIa, digestions of crosslinked fibrin yield a variety of products of various sizes, the smallest of which is D-Dimer (240 kDa). The D domains and the E domain of D-Dimer can be separated by urea extraction resulting in fragment DD (190 kDa) and E (50 kDa).

The following description is merely intended to illustrate various embodiments of the present disclosure. As such, the specific modifications discussed are not intended to be limiting. It will be apparent to one skilled in the art that various equivalents, changes, and modifications may be made without departing from the spirit or scope of the subject matters presented herein, and it is understood that such equivalent embodiments are to be included herein.

As used in this specification and the appended claims, the singular forms "a," "an" and "the" include plural references unless the content clearly dictates otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Unless otherwise defined, all technical and scientific terms used herein have the same meaning as commonly understood by one of ordinary skill in the art to which this invention pertains. Exemplary methods and materials are described below, although methods and materials similar or equivalent to those described herein can also be used and will be apparent to those of skill in the art. All publications and other references mentioned herein are incorporated by reference in their entirety. In case of conflict, the present specification, including definitions, will control. The materials, methods, and examples are illustrative only and not intended to be limiting.

Each embodiment in this specification is to be applied mutatis mutandis to every other embodiment unless expressly stated otherwise.

The following terms, unless otherwise indicated, shall be understood to have the following meanings:

As used herein, the term "nucleic acid" refers to any materials comprised of DNA or RNA. Nucleic acids can be made synthetically or by living cells.

As used herein, the term "polynucleotide" refers to a polymeric chain of nucleotides. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native inter-nucleoside bonds, or both. The nucleic acid can be in any topological conformation. For instance, the nucleic acid can be single-stranded, double-stranded, triple-stranded, quadruplexed, partially double-stranded, branched, hair-pinned, circular, or in a padlocked conformation.

As used herein, the term "protein" or refers to large biological molecules, or macromolecules, consisting of one or more chains of amino acid residues. Many proteins are enzymes that catalyze biochemical reactions and are vital to metabolism. Proteins also have structural or mechanical functions, such as actin and myosin in muscle and the proteins in the cytoskeleton, which form a system of scaffolding that maintains cell shape. Other proteins are important in cell signaling, immune responses, cell adhesion, and the cell cycle. However, proteins may be completely artificial or recombinant, i.e., not existing naturally in a biological system.

As used herein, the term "polypeptide" refers to both naturally-occurring and non-naturally-occurring proteins, and fragments, mutants, derivatives and analogs thereof. A polypeptide may be monomeric or polymeric. A polypeptide may comprise a number of different domains (peptides) each of which has one or more distinct activities.

As used herein, the term "recombinant" refers to a biomolecule, e.g., a gene or protein, that (1) has been removed from its naturally occurring environment, (2) is not associated with all or a portion of a polynucleotide in which the gene is found in nature, (3) is operatively linked to a polynucleotide which it is not linked to in nature, or (4) does not occur in nature. The term "recombinant" can be used in reference to cloned DNA isolates, chemically synthesized polynucleotide analogs, or polynucleotide analogs that are biologically synthesized by heterologous systems, as well as proteins and/or mRNAs encoded by such nucleic acids.

As used herein, the term "antigen" refers to a biomolecule that binds specifically to the respective antibody. An antibody from the diverse repertoire binds a specific antigenic structure by means of its variable region interaction.

As used herein, the term "fusion protein" refers to proteins comprising two or more amino acid sequences that do not co-exist in naturally-occurring proteins. A fusion protein may comprise two or more amino acid sequences from the same or from different organisms. The two or more amino acid sequences of a fusion protein are typically in frame without stop codons between them and are typically translated from mRNA as part of the fusion protein.

As used herein, the term "antibody" includes polyclonal antibodies, monoclonal antibodies, multispecific antibodies, human antibodies, humanized antibodies (fully or partially humanized), animal antibodies, recombinant antibodies, chimeric antibodies, and antibody fragments. Thus, the term "antibody fragments" as used herein, include but are not limited to variable fragments (Fv), single-chain Fvs (scFv), bispecific antibodies (sc$(Fv)_2$), single chain antibodies, single domain antibodies, Fab fragments, $F(ab')_2$ fragments, Fab' fragments, disulfide-linked Fv (dsFv), chemically conjugated Fv (ccFv), diabodies and anti-idiotypic (anti-Id) antibodies, and functionally active epitope-binding fragments of any of the above. In certain embodiments antibodies also include affibodies, nanobodies, and unibodies. In certain embodiments particular antibodies include immunoglobulin molecules and immunologically active fragments of immunoglobulin molecules, namely, molecules that contain an antigen binding site. Immunoglobulin molecules can be of any type (for example, IgG, IgE, IgM, IgD, IgA and IgY), class (for example, IgG1, IgG2, IgG3, IgG4, IgAi and IgA2) or subclass.

As used herein, the terms "antigen-binding fragment (Fab)" refers to antibody fragments comprising one constant and one variable domain of each of the heavy and the light chain. The variable domain contains the antigen-binding sites. Generally, an antibody comprises a fragment crystallizable region (Fc) and two antigen-binding fragments (Fab). The Fab fragments can be separated from the Fc region resulting in two Fab fragments, which is also known as $F(ab')_2$ fragment or dimeric fragment antigen binding.

In natural antibodies, two heavy chains are linked to each other by disulfide bonds and each heavy chain is linked to a light chain by a disulfide bond. There are two types of light chain, lambda (A) and kappa (κ). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from non-hypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, normally includes six CDRs, comprising the CDR set from each of a heavy and a light chain V region. Framework Regions (FRs) refer to amino acid sequences interposed between CDRs.

CDRs can be identified in accordance with the definitions of the Kabat, Chothia, the accumulation of both Kabat and Chothia, AbM, contact, IMGT unique numbering, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others (See, e.g., Chothia et al., Nature 342:877-883, 1989). Other approaches to CDR identification include the "AbM definition," which is a compromise between Kabat and Chothia and is derived using Oxford Molecular's AbM antibody modeling software (now Accelrys0), the "contact definition" of CDRs based on observed antigen contacts, set forth in MacCallum et al., J. Mol. Biol., 262:732-745, 1996, or "IMGT unique numbering", which relies on the high conservation of the structure of the variable region (see Lefranc, M.-P. Nucl. Acids Res., 33, D593-D597, 2005). In another approach, referred to herein as the "conformational definition" of CDRs, the positions of the CDRs may be identified as the residues that make enthalpic contributions to antigen binding. See, e.g., Makabe et al., Journal of Biological Chemistry, 283:1156-1166, 2008. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, each CDR may be defined in accordance with any one of Kabat, Chothia, extended, AbM, contact, IMGT unique numbering, or conformational definitions.

Exemplary databases of antibody sequences are described in, and can be accessed through, the "Abysis" website at www.bioinf.org.uk/abs (maintained by A. C. Martin in the Department of Biochemistry & Molecular Biology University College London, London, England) and the VBASE2 website at www.vbase2.org, as described in Retter et al., Nucl. Acids Res., 33 (Database issue): D671-D674 (2005). Preferably sequences are analyzed using the Abysis database, which integrates sequence data from Kabat, IMGT and the Protein Data Bank (PDB) with structural data from the PDB. Unless otherwise indicated, all CDRs set forth herein are derived according to the Abysis database website as per the scheme indicated.

As used herein, the term "monoclonal antibody" refers to an antibody composition having a homogeneous antibody population that bind to the same epitope. The term is not limited regarding the species or source of the antibody, nor is it intended to be limited by the manner in which it is made. Thus, the term encompasses antibodies obtained from murine hybridomas, as well as human monoclonal antibodies obtained using human rather than murine hybridomas.

As used herein, the term “epitope” refers to the portion of an antigen to which an antibody specifically binds. Thus, the term “epitope” includes any protein determinant capable of specific binding to an immunoglobulin or T-cell receptor.

As used herein, the term “recombinant antibody” refers to antibodies or fragments thereof that are non-naturally occurring and can be associated with a polypeptide or fragment thereof that is not found in nature. Recombinant antibodies can be produced by any of the recombinant techniques well known by the skilled person.

As used herein, the terms “identical” or “percent identity,” in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In some embodiments, the two sequences that are compared are the same length after gaps are introduced within the sequences, as appropriate (e.g., excluding additional sequence extending beyond the sequences being compared). For sequence comparisons between two sequences, a “corresponding” CDR refers to a CDR in the same location in both sequences (e.g., CDR-H1 of each sequence).

The determination of percent identity or percent similarity between two sequences can be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul et al., 1990, J. Mol. Biol. 215:403-410. BLAST nucleotide searches can be performed with the NBLAST program, score=100, wordlength=12, to obtain nucleotide sequences homologous to a nucleic acid encoding a protein of interest. BLAST protein searches can be performed with the XBLAST program, score=50, wordlength=3, to obtain amino acid sequences homologous to protein of interest. To obtain gapped alignments for comparison purposes, Gapped BLAST can be utilized as described in Altschul et al., 1997, Nucleic Acids Res. 25:3389-3402. When utilizing BLAST and Gapped BLAST the default parameters of the respective programs (e.g., XBLAST and NBLAST) can be used. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

A polypeptide is “immunologically reactive” with an antibody when it binds to an antibody due to antibody recognition of a specific epitope contained within the polypeptide. Immunological reactivity may be determined by antibody binding, more particularly by the kinetics of antibody binding, and/or by competition in binding using as competitor(s) a known polypeptide(s) containing an epitope against which the antibody is directed. The techniques for determining whether a polypeptide is immunologically reactive with an antibody are known in the art.

The term “sample”, as used herein, refers to any biological material obtained from a subject or patient. In one aspect, a sample can comprise blood, peritoneal fluid, CSF, saliva or urine. In other aspects, a sample can comprise whole blood, blood plasma, blood serum, B cells enriched from blood samples, and cultured cells (e.g., B cells from a subject). A sample can also include a biopsy or tissue sample including neural tissue. In still other aspects, a sample can comprise whole cells and/or a lysate of the cells.

The term “Diagnostic” or “diagnosed”, as used herein, means identifying the presence or nature of a pathologic condition or a patient susceptible to a disease. Diagnostic methods differ in their sensitivity and specificity. The “sensitivity” of a diagnostic assay is the percentage of diseased individuals who test positive (percent of “true positives”). Diseased individuals not detected by the assay are “false negatives.” Subjects who are not diseased and who test negative in the assay, are termed “true negatives.” The “specificity” of a diagnostic assay is 1 minus the false positive rate, where the “false positive” rate is defined as the proportion of those without the disease who test positive. While a particular diagnostic method may not provide a definitive diagnosis of a condition, it suffices if the method provides a positive indication that aids in diagnosis.

The terms “patient” or “individual” are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

DETAILED DESCRIPTION

I. Recombinant Antibodies

The present invention relates to an anti-D-dimer recombinant antibody that specifically binds to fibrin and fibrinogen degradation products (FDP) D-Dimer, fragment DD and fragment D and it does not bind to fragment E and fibrinogen.

In one embodiment described herein, the recombinant antibody comprises a light chain and a heavy chain. In other embodiment described herein, the recombinant antibody comprises two light chains and two heavy chains. The light chain(s) of the recombinant antibody of the present invention can comprise two domains, a variable domain (VL) and a constant domain (CL). The heavy chain(s) of the recombinant antibody of the present invention can comprise four domains, a variable domain (VH) and three constant domains (CH1, CH2 and CH3, collectively referred to as CH).

In another embodiment, the recombinant antibody of the present invention is a monoclonal antibody or an antibody fragment. In a preferred embodiment, said antibody fragment is selected from variable fragments (Fv), single-chain Fvs (scFv), bispecific antibodies (sc$(Fv)_2$), single chain antibodies, single domain antibodies, Fab fragments, $F(ab')_2$ fragments, Fab' fragments, disulfide-linked Fv (dsFv), chemically conjugated Fv (ccFv), diabodies, anti-idiotypic (anti-Id) antibodies, affibodies, nanobodies, and unibodies.

In one embodiment described herein, the recombinant antibody comprises the Fc region and the two Fab fragments. In other embodiment described herein, the recombinant antibody is a fragment antigen binding and does not comprises the Fc region. In other embodiment described herein, the recombinant antibody consists of one Fab fragment. In other embodiment described herein, the recombinant antibody consists of two Fab fragments ($F(ab)_2$).

In one embodiment described herein, the recombinant antibody may be of any known type (for example, IgG, IgE, IgM, IgD, IgA and IgY), or any known class (for example, IgG1, IgG2, IgG3, IgG4, IgAi and IgA2) or any known subclass.

In one embodiment described herein, the recombinant antibody is of the IgG type. In a preferred embodiment, the recombinant antibody is of the IgG1, IgG2, IgG3 or IgG4 class. In another preferred embodiment, the recombinant antibody is of the IgG1 or IgG2 class. In another preferred embodiment, the recombinant antibody is of the IgG2a class.

In the most preferred embodiment, the recombinant antibody of the present invention comprises a constant region of the murine IgG1 class or the murine IgG2a class.

A. Light Chain

In one embodiment described herein, the recombinant antibody comprises a light chain comprising complementary determining regions (CDR). Said CDRs correspond to the sequences identified according to any CDR definition approach known by the skilled person. In some preferred embodiments, the CDRs regions correspond to the sequences identified according to Kabat. In some preferred embodiments, the CDRs regions correspond to the sequences identified according to Chothia. In another embodiment, the CDRs may be any of Kabat, Chothia, AbM, extended, contact, IMGT unique numbering and/or conformational definitions, combination CDRs, or combinations thereof.

In one embodiment described herein, the recombinant antibody comprises a light chain comprising complementary determining regions L-CDR1, L-CDR2 and L-CDR3, each of them comprising a (distinct) sequence of at least five contiguous amino acids selected from the amino acid sequence of SEQ ID NO: 18. In one preferred embodiment, said at least five contiguous amino acids selected from the amino acid sequence of SEQ ID NO: 18 include at least one of amino acids 24 to 34, or 50 to 56 or 89 to 97 of SEQ ID NO: 18. In one embodiment, said L-CDR1, L-CDR2 and L-CDR3 of the light chain comprise the amino acid sequences of SEQ ID NO: 31, SEQ ID NO: 32, and SEQ ID NO: 33 respectively. In this embodiment, SEQ ID NOS: 31 to 33 represent the Kabat defined L-CDR1, L-CDR2, and L-CDR3 respectively of SEQ ID NO: 18.

In another embodiment described herein, the variable region of the light chain of the recombinant antibody of the present invention comprises the amino acid sequence of SEQ ID NO: 18 or a fragment thereof. In yet another embodiment, the variable region of the light chain of the recombinant antibody may have about 70%, 75%, 80%, 85%, 90%, 91%, 92%, 93%, 94%, 95%, 96%, 97%, 98%, 99% or more homology to the amino acid sequence consisting of SEQ ID NO: 18.

In another embodiment described herein, the recombinant antibody comprises a light chain comprising the amino acid sequence of SEQ ID NO: 17 or SEQ ID NO: 18 or a fragment thereof. In other embodiment, the light chain of the recombinant antibody may have about 70%, 75%, 80%, 85%, 90%, 91%, 92%, 93%, 94%, 95%, 96%, 97%, 98%, 99% or more homology to the amino acid sequence consisting of SEQ ID NO: 17 or SEQ ID NO: 18.

B. Heavy Chain

In one embodiment described herein, the recombinant antibody comprises a heavy chain comprising complementary determining regions (CDR). Said CDRs correspond to the sequences identified according to any CDR definition approach known by the skilled person. In some preferred embodiments, the CDRs regions correspond to the sequences identified according to Kabat. In some preferred embodiments, the CDRs regions correspond to the sequences identified according to Chothia. In another embodiment, the CDRs may be any of Kabat, Chothia, AbM, extended, contact, IMGT unique numbering and/or conformational definitions, combination CDRs, or combinations thereof.

In one embodiment described herein, the recombinant antibody comprises a heavy chain comprising complementary determining regions H-CDR1, H-CDR2 and H-CDR3, each of them comprising a sequence of at least five contiguous amino acids selected from the amino acid sequence of SEQ ID NO: 19, or SEQ ID NO: 20, or SEQ ID NO: 21 or SEQ ID NO: 22. In a preferred embodiment, said at least five contiguous amino acids selected from the amino acid sequence of SEQ ID NO: 19, or SEQ ID NO: 20, or SEQ ID NO: 21 or SEQ ID NO: 22 include at least one of amino acids 31 to 35, or 50 to 65 or 95 to 102 of SEQ ID NO: 19, or of SEQ ID NO: 20, or of SEQ ID NO: 21, or of SEQ ID NO: 22. In one preferred embodiment said H-CDR1, H-CDR2 and H-CDR3 of the heavy chain may comprise the amino acid sequences of SEQ ID NO: 34, SEQ ID NO: 35, and SEQ ID NO: 36 respectively. In this embodiment, SEQ ID NOS: 34 and 36 represent the H-CDR1 and H-CDR3 respectively of SEQ ID NOS: 19 to 22 as determined by Kabat, and SEQ ID NO: 35 represents the H-CDR2 of SEQ ID NOS: 19 to 22 as determined by Chothia.

In a further embodiment, the heavy chain may comprise complementary determining regions H-CDR1, H-CDR2, and H-CDR3 as defined by SEQ ID NOS: 34, 37, and 36 respectively. In this embodiment, SEQ ID NOS: 34, 37, and 36 represent the Kabat defined H-CDR1, H-CDR2, and H-CDR3 respectively of SEQ ID NOS: 19 to 20.

In yet a further embodiment, the heavy chain may comprise complementary determining regions H-CDR1, H-CDR2, and H-CDR3 as defined by SEQ ID NOS: 34, 38, and 36 respectively. In this embodiment, SEQ ID NOS: 34, 38, and 36 represent the Kabat defined H-CDR1, H-CDR2, and H-CDR3 respectively of SEQ ID NOS: 21 to 22.

In another embodiment described herein, the variable region of a heavy chain of the recombinant antibody of the present invention comprises the amino acid sequence of SEQ ID NO: 19, SEQ ID NO: 20, SEQ ID NO: 21 or SEQ ID NO: 22 or a fragment thereof. In other embodiment, the variable region of the light chain of the recombinant antibody may have about 70%, 75%, 80%, 85%, 90%, 91%, 92%, 93%, 94%, 95%, 96%, 97%, 98%, 99% or more homology to the amino acid sequence consisting of SEQ ID NO: 19, SEQ ID NO: 20, SEQ ID NO: 21 or SEQ ID NO: 22.

In another embodiment described herein, the recombinant antibody comprises a heavy chain comprising the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO:16, SEQ ID NO: 19, SEQ ID NO: 20, SEQ ID NO: 21 or SEQ ID NO: 22, or a fragment thereof. In other embodiment, the light chain of the recombinant antibody may have about 70%, 75%, 80%, 85%, 90%, 91%, 92%, 93%, 94%, 95%, 96%, 97%, 98%, 99% or more homology to the amino acid sequence consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO:16, SEQ ID NO: 19, SEQ ID NO: 20, SEQ ID NO: 21 or SEQ ID NO: 22.

C. Affinity Tags

A recombinant antibody according to the present invention may optionally include an affinity tag. Affinity tags are useful for purification. Exemplary affinity tags include polyhistidine, Glutathione S-transferase (GST), chitin binding protein, maltose binding protein (MBP), streptavidin binding peptide (Strep-tag), isopeptide bond forming, FLAG-tag, V5-tag, Myc-tag, HA-tag, NE-tag, AviTag, Calmodulin-tag, polyglutamate, S-tag, SBP-tag, Softag 1, Softag 3, TC tag, VSV-tag, Xpress tag, Isopeptag, SpyTag, SnoopTag, biotin carboxyl carrier protein, green fluorescent protein-tag, HaloTag, Nus-tag, and thioredoxin-tag, although the choice of affinity tag is not particularly limiting. A recombinant antibody may nevertheless lack an affinity tag, for example, if the affinity tag is removed after use or if the recombinant antibody is purified using a strategy that does not require an affinity tag. An exemplary affinity tag is polyhistidine, which typically includes an amino acid sequence comprising between 4 and 10 consecutive histidines. A preferred affinity tag is a polyhistidine tag comprising between 6 to 10 consecutive histidines. Exemplary affinity tags correspond to SEQ ID NO: 23, SEQ ID NO: 24 or SEQ ID NO: 25.

The recombinant antibodies of the present invention may optionally include an affinity tag and may optionally be purified using said affinity tag. Several methods of purification recombinant antibodies are available in the state of the art and the skilled person is well aware of them. Exemplary methods of purification for recombinant antibodies, comprising or not an affinity tags, are immobilized metal affinity chromatography (IMAC), Protein NG affinity, exchange chromatography (IEX or IEC), hydrophobic interaction chromatography (HIC) and/or additional use of tags and affinity chromatography techniques beyond IMAC or Protein NG. The purification method and tags utilized should not be considered limiting.

In a preferred embodiment, the recombinant antibody of the present invention further comprises an affinity tag. Said affinity tag can be selected from the group consisting of SEQ ID NO: 23, SEQ ID NO: 24, or SEQ ID NO: 25.

D. Exemplary Recombinant Antibodies

In one embodiment described herein, the recombinant antibody comprises the amino acid sequence of SEQ ID NO: 17.

In one embodiment described herein, the recombinant antibody comprises the amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO:16.

In a preferred embodiment described herein, the recombinant antibody comprises the amino acid sequence of SEQ ID NO: 17 and the amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO:16.

In a most preferred embodiment described herein, the recombinant antibody comprises the amino acid sequence of SEQ ID NO: 17 and the amino acid sequence of SEQ ID NO: 12.

In another preferred embodiment, the light chain of the recombinant antibody may have about 70%, 75%, 80%, 85%, 90%, 91%, 92%, 93%, 94%, 95%, 96%, 97%, 98%, 99% or more homology to the amino acid sequence consisting of SEQ ID NO: 17 and the light chain of the recombinant antibody may have about 70%, 75%, 80%, 85%, 90%, 91%, 92%, 93%, 94%, 95%, 96%, 97%, 98%, 99% or more homology to the amino acid sequence consisting of SEQ ID NO: 12.

In one embodiment, the recombinant antibody of the present invention is bound to a solid support.

In another embodiment, the binding affinity of the recombinant antibody of the present invention with fragment DD is at least 3 times tighter than the binding affinity of said recombinant antibody with fragment D.

III. Nucleic Acids, Cloning Cells, and Expression Cells

The present invention also relates to nucleic acids comprising a nucleotide sequence encoding the recombinant antibodies described herein. The nucleic acid may be DNA or RNA. DNA comprising a nucleotide sequence encoding a recombinant antibody described herein typically comprises a promoter that is operably-linked to the nucleotide sequence. The promoter is preferably capable of driving constitutive or inducible expression of the nucleotide sequence in an expression cell of interest. Said nucleic acid may also comprise a selectable marker useful to select the cell containing said nucleic acid of interest. Useful selectable markers are well known by the skilled person. The precise nucleotide sequence of the nucleic acid is not particularly limiting so long as the nucleotide sequence encodes a recombinant antibody described herein. Codons may be selected, for example, to match the codon bias of an expression cell of interest (e.g., a mammalian cell such as a human cell) and/or for convenience during cloning. DNA may be a plasmid, for example, which may comprise an origin of replication (e.g., for replication of the plasmid in a prokaryotic cell).

In one embodiment described herein, the nucleic acid comprises a nucleotide sequence encoding the recombinant antibody of the present invention, a promoter operably linked to the nucleotide sequence and a selectable marker.

Various aspects of the present invention also relate to a cell comprising a nucleic acid comprising a nucleotide sequence that encodes a recombinant antibody as described herein. The cell may be an expression cell or a cloning cell. Nucleic acids are typically cloned in *E. coli*, although other cloning cells may be used.

If the cell is an expression cell, the nucleic acid is optionally a nucleic acid of a chromosome, i.e., wherein the nucleotide sequence is integrated into the chromosome, although then nucleic acid may be present in an expression cell, for example, as extrachromosomal DNA or vectors, such as plasmids, cosmids, phages, etc. The format of the vector should not be considered limiting.

In one embodiment described herein, the cell is typically an expression cell. The nature of the expression cell is not particularly limiting. Mammalian expression cells may allow for favorable folding, post-translational modifications, and/or secretion of a recombinant antibody or oligomeric recombinant antibody, although other eukaryotic cells or prokaryotic cells may be used as expression cells. Exemplary expression cells include TunaCHO, ExpiCHO, Expi293, BHK, NSO, Sp2/0, COS, C127, HEK, HT-1080, PER.C6, HeLa, and Jurkat cells. The cell may also be selected for integration of a vector, more preferably for integration of a plasmid DNA.

The recombinant antibodies of the present invention can be produced by appropriate transfection strategy of the nucleic acids comprising a nucleotide sequence that encodes the recombinant antibodies into mammalian cells. The skilled person is aware of the different techniques available for transfection of nucleic acids into the cell line of choice (lipofection, electroporation, etc). Thus, the choice of the mammalian cell line and transfection strategy should not be considered limiting. The cell line could be further selected for integration of the plasmid DNA.

In one preferred embodiment described herein, the cell comprises the recombinant antibody of the present invention.

IV. Compositions and Methods Related to Assays

Various aspects of the present invention relate to compositions comprising a recombinant antibody as described herein.

In one embodiment described herein, the composition comprises the recombinant antibody of the present invention and a solid support.

In other embodiment, the composition comprises the recombinant antibody of the present invention and a solid support, wherein the recombinant antibody is covalently or non-covalently bound to the solid support. The term "non-covalently bound," as used herein, refers to specific binding such as between an antibody and its antigen, a ligand and its receptor, or an enzyme and its substrate, exemplified, for example, by the interaction between streptavidin binding protein and streptavidin or an antibody and its antigen.

In other embodiment, the composition comprises the recombinant antibody of the present invention and a solid support, wherein the recombinant antibody is directly or indirectly bound to a solid support. The term "direct" binding, as used herein, refers to the direct conjugation of a molecule to a solid support, e.g., a gold-thiol interaction that binds a cysteine thiol of a recombinant antibody to a gold surface. The term "indirect" binding, as used herein, includes the specific binding of a recombinant antibody to another molecule that is directly bound to a solid support, e.g., a recombinant antibody may bind an antibody that is directly bound to a solid support thereby indirectly binding the recombinant antibody to the solid support. The term "indirect" binding is independent of the number of molecules between the recombinant antibody and the solid support so long as (a) each interaction between the daisy chain of molecules is a specific or covalent interaction and (b) a terminal molecule of the daisy chain is directly bound to the solid support.

A solid support may comprise a particle, a bead, a membrane, a surface, a polypeptide chip, a microtiter plate, or the solid-phase of a chromatography column. For example, the solid support may be a latex bead.

A composition may comprise a plurality of beads or particles, wherein each bead or particle of the plurality of beads or particles are directly or indirectly bound to at least one recombinant antibody as described herein. A composition may comprise a plurality of beads or particles, wherein each bead or particle of the plurality of beads or particles are covalently or non-covalently bound to at least one recombinant antibody as described herein.

Various aspects of the embodiments relate to a kit for detecting the presence of D-Dimer, fragment DD and/or fragment D in a sample, said kit comprising a recombinant antibody and a solid support or composition as described herein.

The compositions and kits described herewith can be either for use in an assay or in compositions that are generated during the performance of an assay. Various aspects of the invention relate to a diagnostic medical device comprising a composition as described herein.

Various aspects of the invention relate to assays. An assay may be an assay for measuring the relative binding affinity of the recombinant antibody of the present invention to D-Dimer, fragment DD and/or fragment D in a sample (e.g., relative to one or more control samples or standards). An assay may be an assay for measuring the relative binding affinity of the recombinant antibody of the present invention to any fribrin(ogen) degradation product (e.g., relative to one or more control samples or standards).

Assays typically feature a solid support that either allows for measurement, such as by turbidimetry, nephelometry, UV/Vis/IR spectroscopy (e.g., absorption, transmission), fluorescence or phosphorescence spectroscopy, or surface plasmon resonance, or aids in the separation of components that directly or indirectly bind the solid support from components that do not directly or indirectly bind the solid support, or both. For example, an assay may include a composition comprising particles or beads, which allow for measurement by turbidimetry or nephelometry (e.g., in a coagulation assay) and/or that aid in the mechanical separation of components that directly or indirectly bind the particles or beads.

Other exemplary assays that may include the recombinant antibody or the composition of the present invention includes but it is not limited to ELISA, viscoelastic tests such as Sonoclot, gel technologies, fluorescence assay and other point-of-care testing using any of these techniques.

Various aspects of the invention relate to methods of detecting the presence of D-Dimer, fragment DD and/or fragment D in a sample.

In one embodiment described herein, the method of detecting the presence of D-Dimer, fragment DD and/or fragment D in a sample comprises the following steps:

a) contacting the sample with at least one recombinant antibody described herein for a time and under conditions sufficient for the formation of an antibody/antigen complex, and
b) detecting said antibody/antigen complex.

Various aspects of the invention relate to methods of measuring the binding affinity of D-Dimer, fragment DD and/or fragment D in a sample.

In one embodiment described herein, the method of measuring the binding affinity of D-Dimer, fragment DD and/or fragment D in a sample comprises the following steps:

a) contacting the sample with at least one recombinant antibody described herein for a time and under conditions sufficient for the formation of an antibody/antigen complex, and
b) determining the binding affinity between the antibody and D-Dimer, fragment DD and/or fragment D in the sample.

Various aspects of the invention relate to methods of measuring the concentration of D-Dimer, fragment DD and/or fragment D in a sample.

In one embodiment described herein, the method of measuring the amount of D-Dimer, fragment DD and/or fragment D in a sample comprises the following steps:

a) contacting the sample with at least one recombinant antibody described herein for a time and under conditions sufficient for the formation of an antibody/antigen complex, and
b) measuring the concentration of D-Dimer, fragment DD and/or fragment D in the sample.

EXEMPLIFICATION

Example 1: Immunization Strategy and Selection of Monoclonal Antibodies

Female Balb/c mice were primed subcutaneously with 50 μg purified D-Dimer in 0.2 mL of saline which was mixed with 0.1 M of complete Freund's adjuvant. On the fourth and second days before fusion, mice were boosted intraperitoneally with the same amount of antigen in saline. P3X63-Ag8-6.5.3 myeloma cells were fused with spleen cells from immunized Balb/c mice. The cell culture supernatants were screened for antibodies specific to purified fragment D from fibrinogen or non-crosslinked fibrin and D-Dimer. Clones producing antibodies specific to D-Dimer but not fibrinogen were used for the production of ascetic fluid in pristine primed Balb/c mice. The IgG fraction of the monoclonal antibodies was purified from ascetic fluid by affinity chromatography on protein A sepharose[11,12].

Example 2: De Novo MS/MS Sequencing of Selected Monoclonal Antibodies

The monoclonal antibodies selected in example 1 were further subjected to de novo MS/MS sequencing.

Briefly, purified antibodies were first confirmed by Intact Mass Spectrometry. Each mAb was then reduced to separate the Heavy Chain (HC) and Light Chain (LC) which were separately digested by a suite of enzymes (trypsin, chymotrypsin, etc.) The bottom-up MS/MS data was collected giving information about the digested peptides and about the b and y ions further identifying the individual amino acids within the peptide for assembly. The information was then processed and the amino acid sequences of the heavy and light chains of the monoclonal antibodies were established.

In total, the sequences of 16 antibodies were established. The respective sequences for each antibody are disclosed below.

| Antibody | Light chain | Heavy Chain |
|---|---|---|
| #1 | SEQ ID NO: 17 | SEQ ID NO: 1 |
| #2 | SEQ ID NO: 17 | SEQ ID NO: 2 |
| #3 | SEQ ID NO: 17 | SEQ ID NO: 3 |
| #4 | SEQ ID NO: 17 | SEQ ID NO: 4 |
| #5 | SEQ ID NO: 17 | SEQ ID NO: 5 |
| #6 | SEQ ID NO: 17 | SEQ ID NO: 6 |
| #7 | SEQ ID NO: 17 | SEQ ID NO: 7 |
| #8 | SEQ ID NO: 17 | SEQ ID NO: 8 |
| #9 | SEQ ID NO: 17 | SEQ ID NO: 9 |
| #10 | SEQ ID NO: 17 | SEQ ID NO: 10 |
| #11 | SEQ ID NO: 17 | SEQ ID NO: 11 |
| #12 | SEQ ID NO: 17 | SEQ ID NO: 12 |
| #13 | SEQ ID NO: 17 | SEQ ID NO: 13 |
| #14 | SEQ ID NO: 17 | SEQ ID NO: 14 |
| #15 | SEQ ID NO: 17 | SEQ ID NO: 15 |
| #16 | SEQ ID NO: 17 | SEQ ID NO: 16 |

Example 3: Transient Expression and Purification of Recombinant Antibodies

Single transfection of multicistronic vector containing both the HC and LC or dual transfection of vectors containing either the HC or LC were performed to generate the desired antibodies or antigen-binding fragment. Tricistronic vectors using the internal ribosome entry site (IRES) sequence from encephalomyocarditis virus (ECMV) were used.

A set of vectors with LC only, HC only, LC-IRES-HC, and HC-IRES-LC were compared, and the highest producer of the desired antibody was selected. The highest antibody producer was the LC-IRES-HC. Additionally, multiple signal peptides were used to generate the desired antibody (Sequence Listing). For the tricistronic vector the IL2 signal peptide was utilized with both the LC and HC.

During stable cell line development, ExpiCHO cells were transfected with the tricistronic vector and selected using both G418 and Neomycin. Two rounds of limiting dilution cloning were used to isolate clonal cell lines. The second round of limiting dilution cloning was imaged to support clonality. During stable cell line development, the cells were assessed for viability and productivity of the desired antibody.

Purification of the recombinant antibodies of interest was done for full length antibodies by either protein A or protein G purification. For antibodies lacking the Fc region (Fab and $F(ab')_2$ formats), a C-terminal fusion of His tag on the HC was added, allowing for IMAC purification followed by SEC polishing.

Example 4: Characterization of Produced Antibodies

SDS-PAGE

Figure 2:
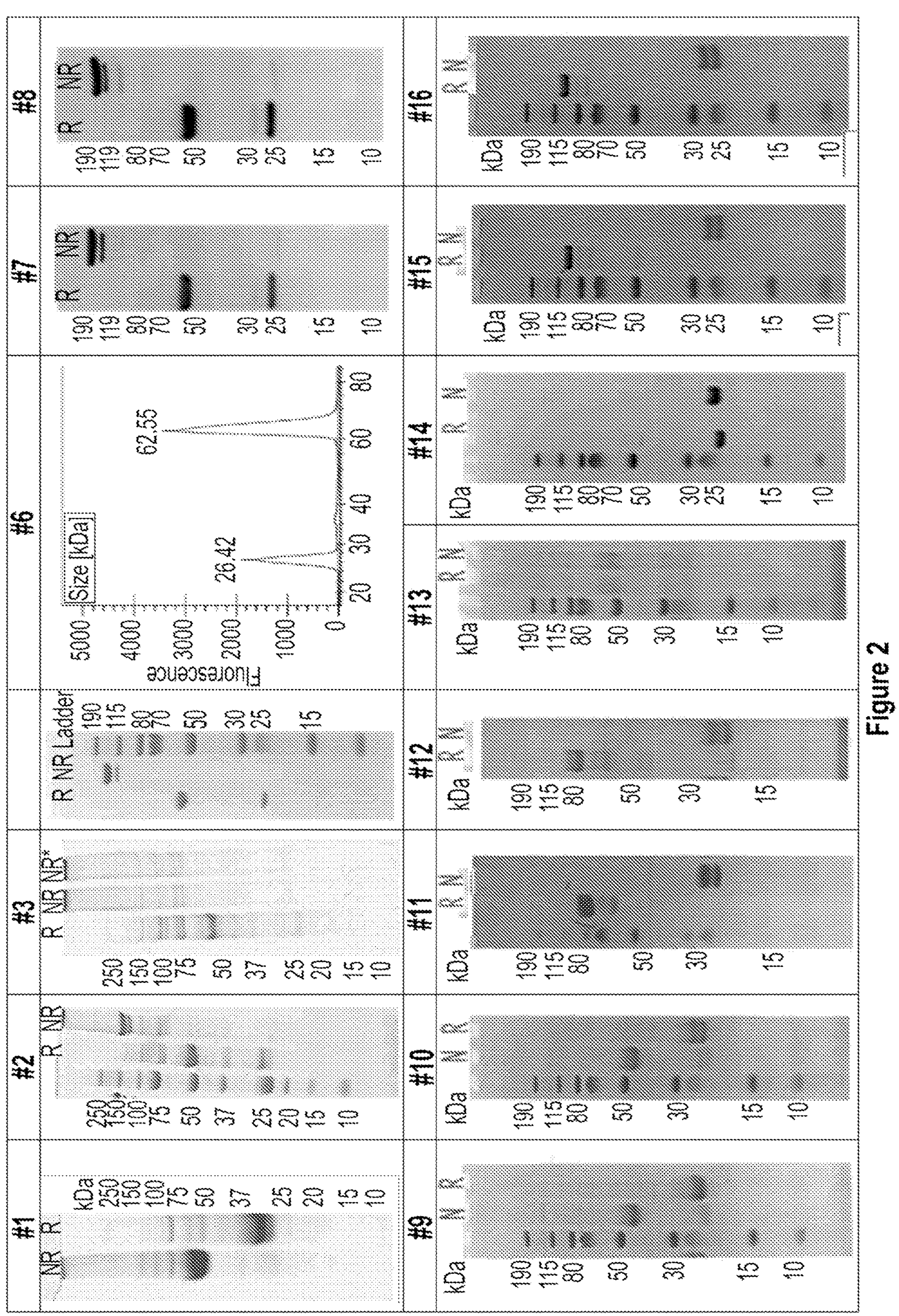
FIG. 2 shows the SDS-PAGE results for recombinant antibodies of the present invention under reducing (R) and non-reducing conditions (N or NR) with the exception of antibodies #4 and #6, for which the result of CE-SDS is shown instead.

Production of each recombinant antibody was verified by SDS-PAGE under reducing and non-reducing conditions (with the exception of antibody #4 (no protein) and #6 (characterized by CE-SDS)) (FIG. 2).

In all cases, the intact antibody can be seen in non-reducing conditions and the respective HC and LC can be seen under reducing conditions. For antibodies #1-3 low production was observed, while no production was shown for #4.

SEC-MALS

Figure 3:
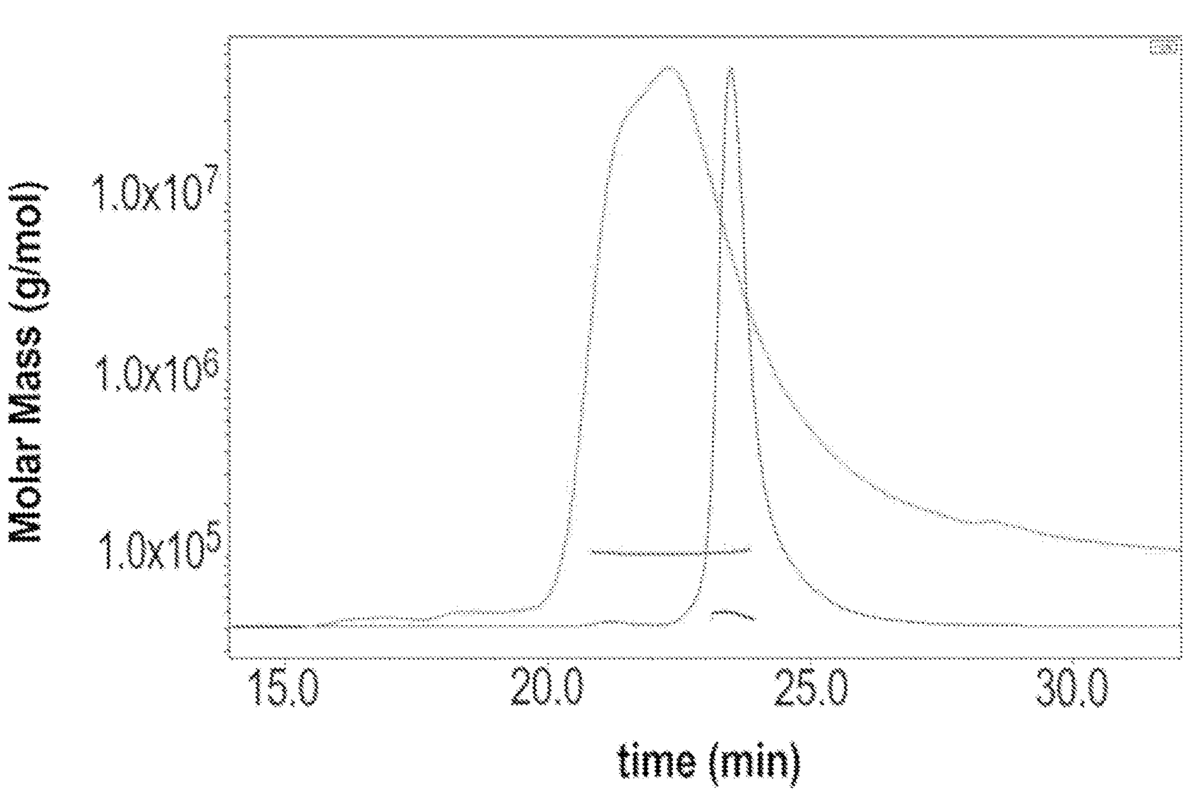
FIG. 3 shows representative light scattering data for antibodies #9 and #12. The A280 trace peaks are intersected by the measure molar mass of each peak and the flat molar mass data across each peak is indicative of a monodisperse sample. #9: predicted mass=48.8 kDa, measured mass=48.3±1% kDa with Mw/Mn=1.001. #12: predicted mass=103 kDa, measured mass=105±4% kDa with Mw/Mn=1.000. All recombinant anti D-Dimer antibodies showed monodisperse peaks (data not shown).

In order to assess the assembly and aggregation of the anti D-Dimer recombinant antibodies of the present invention, size exclusion multi-angle light scattering (SEC-MALS) was employed. SEC-MALS provides the molecular weight and characterizes the polydispersity (Mw/Mn). During the generation of the antibodies, the purified protein was found to be monodisperse with a 1-2% difference. FIG. 3 provides example data for antibodies #9 and #12.

For the anti D-Dimer antibodies, NHS and EDAC chemistries have been used to conjugate the protein to latex beads.

Bio-Layer Interferometry (BLI)

Figure 4:
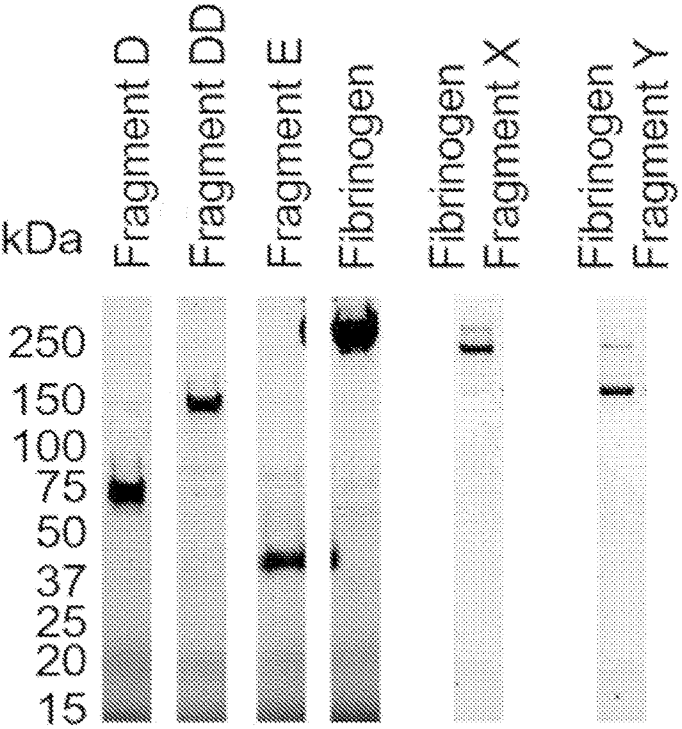
FIG. 4 shows purified FDPs used in binding studies.

Prior to BLI testing, human plasma derived Fragment D, DD, E, fibrinogen, fibrinogen fragment X and fibrinogen fragment Y were characterized in house by SDS-PAGE and further purified by SEC (Superdex 200 Increase 10/300 GL) if visible contaminants were present. Of the fragments mentioned, several were generated in-house due to protein amounts too small to SEC purify out contaminants or they were not commercially available. To generate Fibrinogen Fragment X, Fibrinogen Fragment Y, and Fibrinogen Fragment D, 1 mg amounts of Purified Human Fibrinogen (Aniara) was incubated with 2 mM $CaCl_2$, 50 mM Tris-HCl pH 7.4, 100 mM NaCl, and 0.055 U/mL Human Plasmin (HTI). The temperature was set to 37° C. with shaking at 800 RPM for 7 minutes. 1000 KIU/mL Aprotinin (Sigma) is added immediately and the sample is placed at −20° C. until ready for injection onto the SEC column (Superdex 200 Increase 10/300 GL). The collected fractions were kept at a low temperature for the duration of the purification. Selected peak fractions were then run on SDS-PAGE and pooled and concentrated according to MWs corresponding to Fibrinogen Fragment X, Y, and D. An SDS-PAGE gel of the purified human plasma proteins is available in FIG. 4.

FDPs were prepared and run on 4-20% TGX criterion stain-free gels to check quality and purity prior to moving forward with characterization studies.

Following purification a series of Bio-Layer Interferometry (BLI) studies were conducted to establish the binding affinities of the recombinant antibodies of the present invention.

Figure 5:
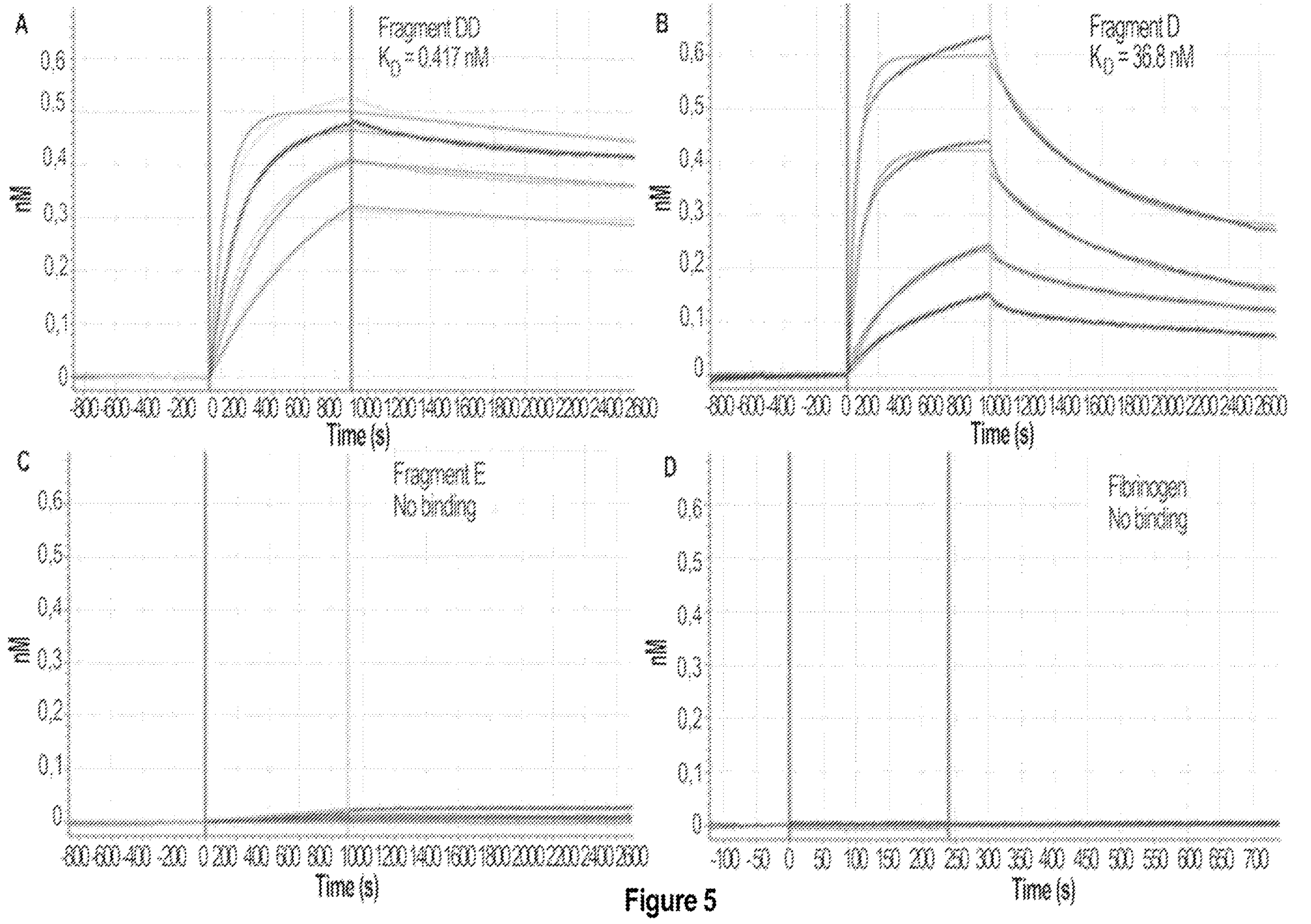
FIG. 5 are graphics showing a comparison of binding affinity of the recombinant antibody #12 with fragments DD, D, E, and fibrinogen. Both fragment DD from fibrin (A) and Fragment D from fibrinogen (B) show binding with antibody #12 when using the Octet BLI platform. Neither Fragment E (C) nor Fibrinogen (D) shows binding with antibody #12.

Binding affinity (at room temperature and pressure) of recombinant antibody #12 was tested with Fragment DD from fibrin, fragment D from fibrinogen, fragment E, and fibrinogen (FIG. 5). Results shown that there is binding with both Fragment DD from fibrin and D from fibrinogen, however the binding with Fragment DD is two orders of magnitude tighter than the binding with Fragment D. These binding properties, specially the difference in binding strength of antibody #12 with fragment DD and with fragment D, have never been reported for hybridoma monoclonal antibodies known in the art[12].

Example 5: Latex Bead Agglutination Assay

Turbidimetric measurements were conducted to assess functions of the recombinant antibodies of the present invention after conjugation to latex beads by standard procedures (such as EDAC and/or NHS chemistries).

Figure 6:
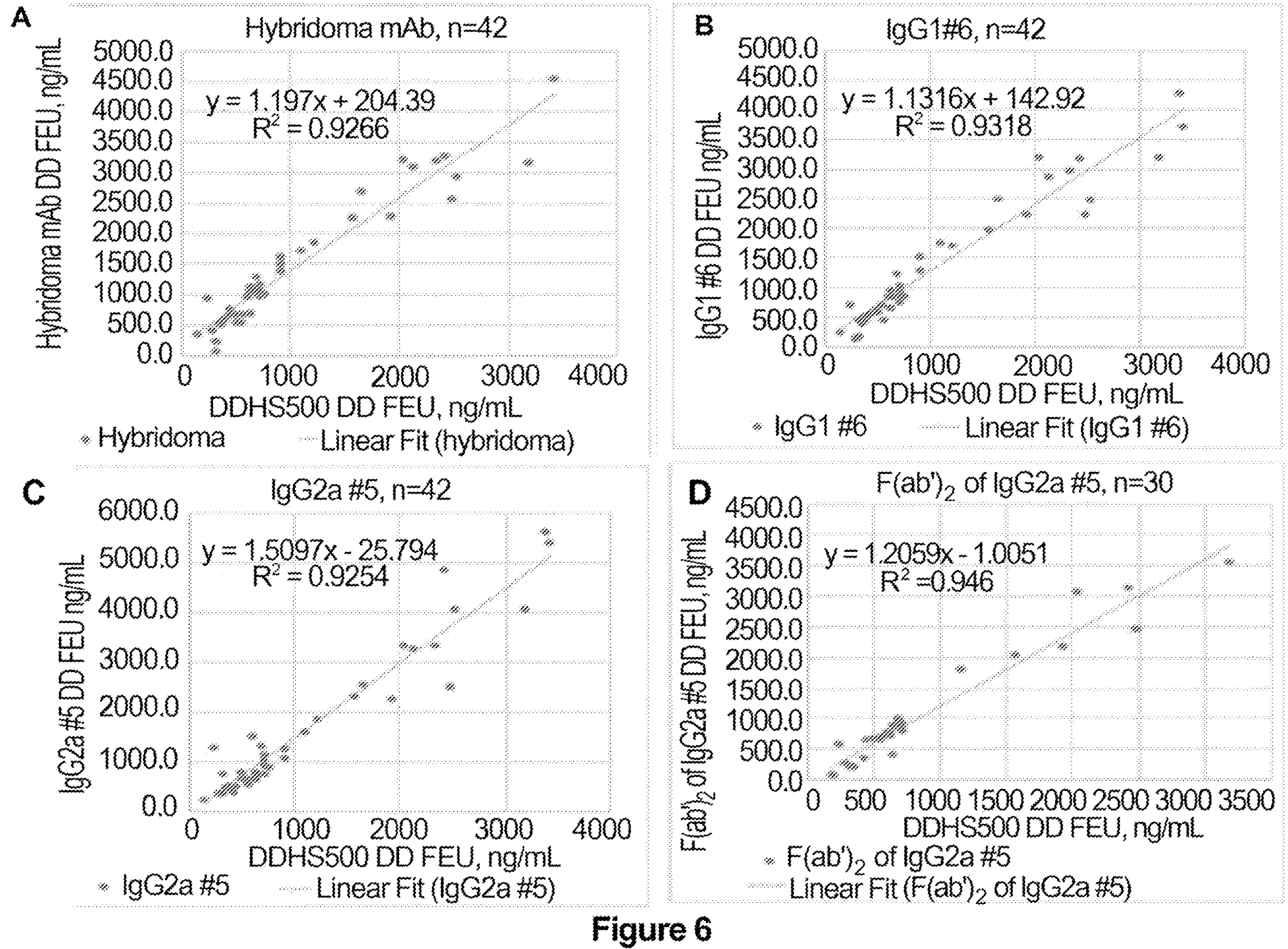
FIG. 6 are graphics showing the presence of D-Dimer in plasma samples correlates well between the HemosIL DDHS500 on the ACL TOP coagulation analyzer with various antibodies on the Q SMART system. A) shows linear correlation using a known 8D3 hybridoma derived antibody, B) shows linear correlation with the IgG1 antibody (#6), C) shows linear correlation with the IgG2a (#5) and D) shows linear correlation using the pepsin digested $F(ab')_2$ of IgG2a #5.

A linear correlation between a known D-Dimer assay, HemosIL DDHS500, and assays developed with the antibodies #6 and #5 exists in all cases indicating D-Dimer in plasma is readily detectable by the antibodies of the present invention during POC assays. The results obtained for antibodies #6 and #5 (FIGS. 6B and 6C) are comparable to known anti-D-Dimer of the state of the art (FIG. 6A). However, a better correlation was shown for the pepsin digested $F(ab')_2$ of IgG2a #5 (FIG. 6D).

Figure 7:
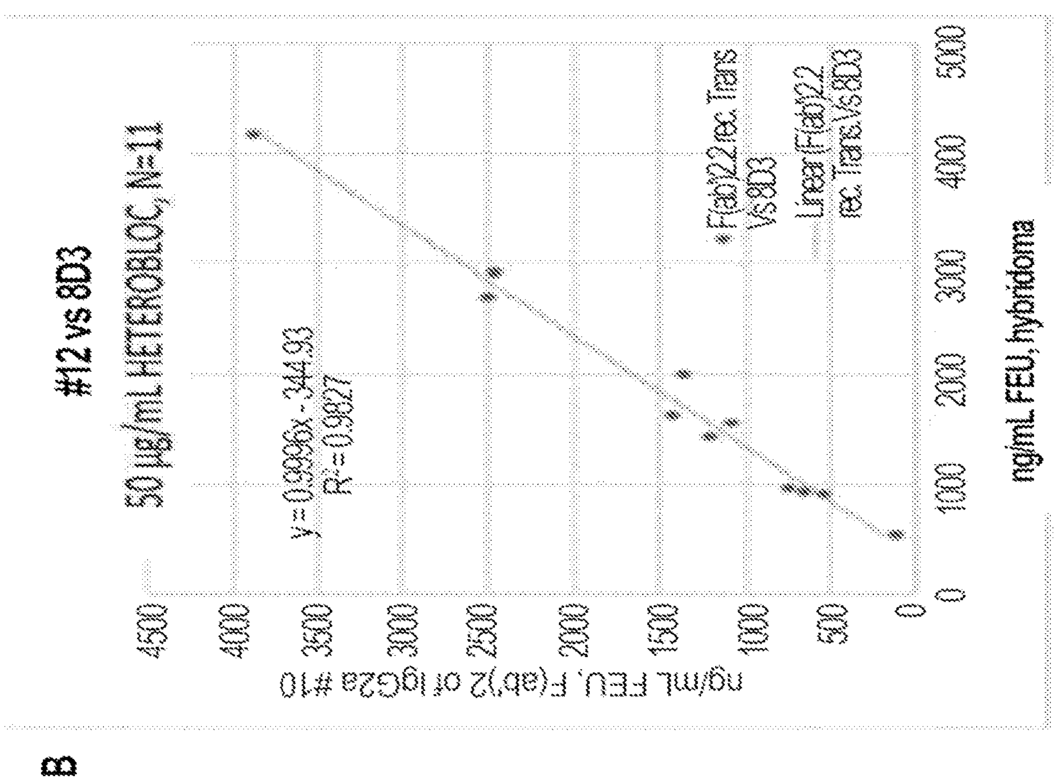
FIG. 7 shows A) linear correlation between #12 and D-dimer using the Grifols Q SMART system with the ACL TOP coagulation analyzer using HemosIL DDHS550 with plasma samples with varying D-Dimer presence, and B) linear correlation when analyzing D-Dimer present in plasma samples using #12 or the hybridoma 8D3 mAb on the Q SMART systems.
Figure 7:
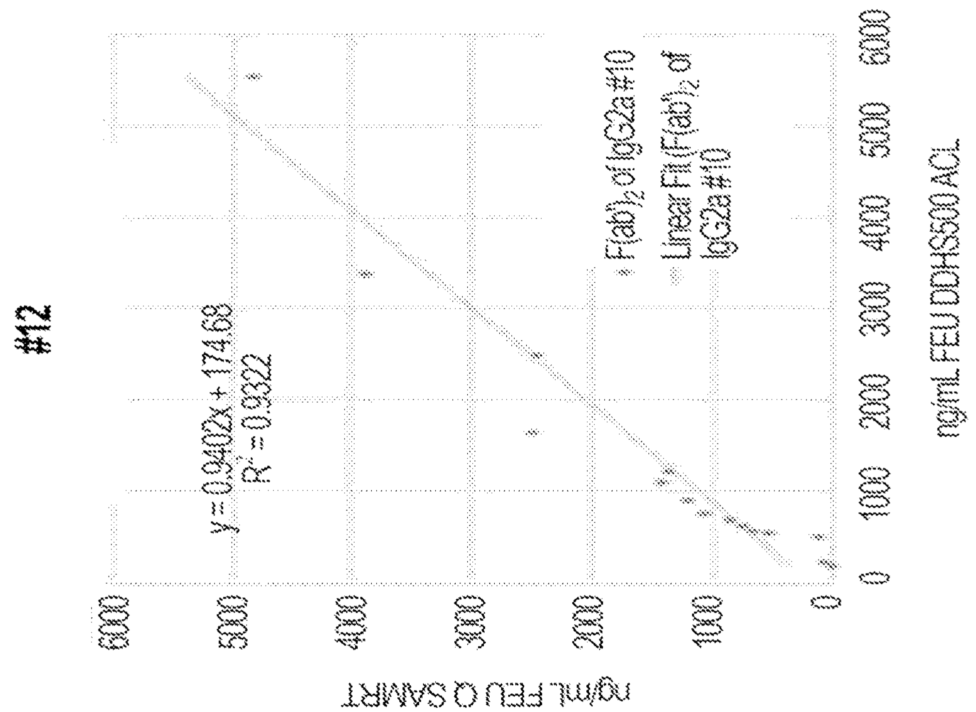

In FIG. 7 it can be seen the correlation between antibody #12 and DDHS500 ACL which shows linear agreement (FIG. 7A) and the antibody #12 with an anti-D-Dimer of the state of the art on the Q SMART platform showing a 1:1 agreement.

Therefore, the present invention provides for recombinant anti D-Dimer antibodies for which their functionality has been assessed both through traditional biophysical measurements (BLI) and by mounting on a latex assay. The results have surprisingly shown that said anti D-Dimer antibodies are different from the antibodies known in the prior art because of their specificity, their binding strength with fragment DD and with fragment D, and the fact that they can be easily produced in mammalian cells thus providing several advantages for latex assay development in comparison with antibodies from hybridoma cell lines, as previously discussed.

Example 6: Epitope Binning Studies

Antibody #12 was compared to other commercially available anti D-Dimer antibodies in binning studies and binding studies to purified fibrin and fibrinogen fragments using the BLI Octet Red96e system from Sartorius. The experiments were conducted at room temperature and pressure. The binning studies were conducted by loading antibody #12, binding to Fragment DD, and then introducing other commercially available mAbs. Response is measured as a nm shift in the interference pattern and is proportional to the number of molecules bound to the surface of the biosensor. The selected mAbs show binding to Fragment DD (see Table 1, units are nm shifted following addition) in the present of antibody #12 suggesting these antibodies recognize different epitopes than antibody #12.

TABLE 1

| | 3B6 | NB110-8376 | DD255 | DCABY-4394 | Ab#12 (Grifols) |
|---|---|---|---|---|---|
| Ab#12 (Grifols) | 0.1362 ± 0.0115 | 0.1731 ± 0.0074 | 0.2232 ± 0.0066 | 0.3944 ± 0.0238 | 0.0759 ± 0.0057 |

The same set of mAbs were subjected to binding studies with fibrinogen, D-Dimer, and purified fibrin and fibrinogen fragments (see Table 2) using the BLI Octet Red96e system from Sartorius. KD was measured by loading biotinylated antibody samples on streptavidin BLI tips and introducing serial dilutions of prepared fragments. KD: ++++ ($10^{-11}$-$10^{-12}$ M); +++ ($10^{-10}$ M); ++ ($10^{-9}$ M); + (≥$10^{-8}$ M). The experiments were conducted at room temperature and pressure.

Grifols antibody #12 showed no binding to fibrinogen or Fragments E from fibrin or fibrinogen, weak binding to fibrinogen fragments X, Y, and D; moderate binding to Fragments X and D; and sub nanomolar binding to D-dimer and fragment DD. In comparison DCABY-4394 showed the tightest binding to D-Dimer and Fragment DD but also tight binding to fibrinogen. 3B6 did not recognize fragment X and showed weaker binding to D-Dimer and fragment DD; NB110-8376 weakly recognized fibrinogen fragments X, Y, but did not recognize D; and DD225 showed weaker binding to fibrin fragments X and D than antibody #12.

TABLE 2

| | | | Fragments | | | | | | | |
|---|---|---|---|---|---|---|---|---|---|---|
| | | | Fibrinogen | | | | Fibrin | | | |
| Ab | D-Dimer | Fibrinogen | X | Y | D | E | X | D | E | DD |
| 3B6 | ++ | − | − | ++ | + | − | ++ | ++ | − | ++ |
| NB110-8376 | ++ | − | + | + | − | − | + | ++ | − | +++ |
| DD255 | +++ | − | + | + | + | − | + | + | − | +++ |
| DCABY-4394 | ++++ | ++++ | ++++ | ++ | ++ | − | ++ | ++ | − | ++++ |
| Ab#12 | +++ | − | + | + | + | − | ++ | ++ | − | +++ |

TABLE 2

SEQUENCE TABLE
Sequences associated with the recombinant antibody of the present invention are outlined below in Table 3.

| Name | Sequence | SEQ ID NO: |
|---|---|---|
| Heavy Chain Ab #1 | QVQLQQPGAEVVRPGASVKLSCQTSGYSFTSYWIHWLKQGPHQGLEWIG<br>RLDPDDSETHYLEKFQGKELLTVDKSSSTAYMQLRSLTSEDSAVYYCARTN<br>WDAWFAYWGQGTLVTASAAKTTPPSVYPLAPGSAAQTNSMVTLGCLVKG<br>YFPEPVTVTWNSGSLSSGVHTFPAVLQSDLYTLSSSVTVPSSTWPSQTVTC<br>NVAHPASSTKVDKKIVPRDCGCKPCICTVPEVSSVFIFPPKPKDVLTITLTPK<br>VTCVVVDISKDDPEVQFSWFVDDVEVHTAQTQPREEQFNSTFRSVSELPIM<br>HQDWLNGKEFKCRVNSAAFPAPIEKTISKTKGRPKAPQVYTIPPPKEQMAK<br>DKVSLTCMITDFFPEDITVEWQWNGQPAENYKNTQPIMDTDGSYFVYSKLN<br>VQKSNWEAGNTFTCSVLHEGLHNHHTEKSLSHSPG | 1 |
| Heavy Chain Ab #2 | QVQLQQPGAEVVRPGASVKLSCQTSGYSFTSYWIHWLKQGPHQGLEWIG<br>RLDPDDSETHYLEKFQGKELLTVDKSSSTAYMQLRSLTSEDSAVYYCARTN<br>WDAWFAYWGQGTLVTASAAKTTPPSVYPLAPGSAAQTNSMVTLGCLVKG<br>YFPEPVTVTWNSGSLSSGVHTFPAVLQSDLYTLSSSVTVPSSTWPSETVTC<br>NVAHPASSTKVDKKIVPRDCGCKPCICTVPEVSSVFIFPPKPKDVLTITLTPK<br>VTCVVVDISKDDPEVQFSWFVDDVEVHTAQTQPREEQFNSTFRSVSELPIM<br>HQDWLNGKEFKCRVNSAAFPAPIEKTISKTKGRPKAPQVYTIPPPKEQMAK<br>DKVSLTCMITDFFPEDITVEWQWNGQPAENYKNTQPIMDTDGSYFVYSKLN<br>VQKSNWEAGNTFTCSVLHEGLHNHHTEKSLSHSPG | 2 |
| Heavy Chain Ab #3 | QVQLQQPGAEVVRPGASVKLSCQTSGYSFTSYWIHWLKQGPHQGLEWIG<br>RLDPDDSETHYLEKFQGKELLTVDKSSSTAYMQLRSLTSEDSAVYYCARTN<br>WDAWFAYWGQGTLVTASAAKTTPPSVYPLAPGSAAQTNSMVTLGCLVKG<br>YFPEPVTVTWNSGSLSSGVHTFPAVLQSDLYTLSSSVTVPSSTWPSETVTC<br>NVAHPASSTKVDKKIVPRDCGCKPCICTVPEVSSVFIFPPKPKDVLTITLTPK<br>VTCVVVDISKDDPEVQFSWFVDDVEVHTAQTQPREEQFNSTFRSVSELPIM<br>HQDWLNGKEFKCRVNSAAFPAPIEKTISKTKGRPKAPQVYTIPPPKEQMAK<br>DKVSLTCMITDFFPEDITVEWQWNGQPAENYKNTQPIMDTDGSYFVYSKLN<br>VQKSNWEAGNTFTCSVLHEGLHNHHTEKSLSHSPG | 3 |
| Heavy Chain Ab #4 | QVQLQQPGAEVVRPGASVKLSCKASGYSFTSYWIHWLKQGPHQGLEWIG<br>RLDPDDSETHYLEKFQGKELLTVDKSSSTAYMQLRSLTSEDSAVYYCARTN<br>WDAWFAYWGQGTLVTVSAAKTTAPSVYPLAPVCGDTTGSSVTLGCLVKG<br>YFPEPVTLTWNSGSLSSGVHTFPAVLQSDLYTLSSSVTVTSSTWPSQSITC<br>NVAHPASSTKVDKKIEPRGPTIKPCPPCKCPAPNLLGGPSVFIFPPKIKDVLM<br>ISLSPIVTCVVVDVSEDDPDVQISWFVNNVEVHTAQTQTHREDYNSTLRVV<br>SALPIQHQDWMSGKEFKCKVNNKDLPAPIERTISKPKGSVRAPQVYVLPPP<br>EEEMTKKQVTLTCMVTDFMPEDIYVEWTNNGKTELNYKNTEPVLDSDGSY<br>FMYSKLRVEKKNWVERNSYSCSVVHEGLHNHHTTKSFSRTPG | 4 |
| Heavy Chain Ab #5 | QVQLQQPGAEVVRPGASVKLSCKASGYSFTSYWIHWLKQGPHQGLEWIG<br>RIDPDDSETHYNQKFKDKALLTVDKSSSTAYMQLRSLTSEDSAVYYCARTN<br>WDAWFAYWGQGTLVTVSAAKTTAPSVYPLAPVCGDTTGSSVTLGCLVKG<br>YFPEPVTLTWNSGSLSSGVHTFPAVLQSDLYTLSSSVTVTSSTWPSQSITCN<br>VAHPASSTKVDKKIEPRGPTIKPCPPCKCPAPNLLGGPSVFIFPPKIKDVLM<br>ISLSPIVTCVVVDVSEDDPDVQISWFVNNVEVHTAQTQTHREDYNSTLRVV<br>SALPIQHQDWMSGKEFKCKVNNKDLPAPIERTISKPKGSVRAPQVYVLPPP<br>EEEMTKKQVTLTCMVTDFMPEDIYVEWTNNGKTELNYKNTEPVLDSDGSY<br>FMYSKLRVEKKNWVERNSYSCSVVHEGLHNHHTTKSFSRTPG | 5 |
| Heavy Chain Ab #6 | QVQLQQPGAEVVRPGASVKLSCKASGYSFTSYWIHWLKQGPHQGLEWIG<br>RIDPDDSETHYNQKFKDKALLTVDKSSSTAYMQLRSLTSEDSAVYYCARTN<br>WDAWFAYWGQGTLVTVSAAKTTPPSVYPLAPGSAAQTNSMVTLGCLVKG<br>YFPEPVTVTWNSGSLSSGVHTFPAVLQSDLYTLSSSVTVPSSTWPSETVTCN<br>VAHPASSTKVDKKIVPRDCGCKPCICTVPEVSSVFIFPPKPKDVLTITLTPK<br>VTCVVVDISKDDPEVQFSWFVDDVEVHTAQTQPREEQFNSTFRSVSELPIM<br>HQDWLNGKEFKCRVNSAAFPAPIEKTISKTKGRPKAPQVYTIPPPKEQMAK<br>DKVSLTCMITDFFPEDITVEWQWNGQPAENYKNTQPIMDTDGSYFVYSKLN<br>VQKSNWEAGNTFTCSVLHEGLHNHHTEKSLSHSPG | 6 |
| Heavy Chain Ab #7 | QVQLQQPGAEVVRPGASVKLSCQTSGYSFTSYWIHWLKQGPHQGLEWIG<br>RIDPDDSETHYNQKFKDKALLTVDKSSSTAYMQLRSLTSEDSAVYYCARTN<br>WDAWFAYWGQGTLVTASAAKTTAPSVYPLAPVCGDTTGSSVTLGCLVKG<br>YFPEPVTLTWNSGSLSSGVHTFPAVLQSDLYTLSSSVTVTSSTWPSQSITCN<br>VAHPASSTKVDKKIEPRGPTIKPCPPCKCPAPNLLGGPSVFIFPPKIKDVLM<br>ISLSPIVTCVVVDVSEDDPDVQISWFVNNVEVHTAQTQTHREDYNSTLRVV<br>SALPIQHQDWMSGKEFKCKVNNKDLPAPIERTISKPKGSVRAPQVYVLPPP<br>EEEMTKKQVTLTCMVTDFMPEDIYVEWTNNGKTELNYKNTEPVLDSDGSY<br>FMYSKLRVEKKNWVERNSYSCSVVHEGLHNHHTTKSFSRTPG | 7 |

TABLE 2-continued

SEQUENCE TABLE
Sequences associated with the recombinant antibody of the present invention are outlined below in Table 3.

| Name | Sequence | SEQ ID NO: |
|---|---|---|
| Heavy Chain Ab #8 | QVQLQQPGAEVVRPGASVKLSCQTSGYSFTSYWIHWLKQGPHQGLEWIG RIDPDDSETHYNQKFKDKALLTVDKSSSTAYMQLRSLTSEDSAVYYCARTN WDAWFAYWGQGTLVTASAAKTTPPSVYPLAPGSAAQTNSMVTLGCLVKG YFPEPVTVTWNSGSLSSGVHTFPAVLQSDLYTLSSSVTVPSSTWPSETVTCN VAHPASSTKVDKKIVPRDCGCKPCICTVPEVSSVFIFPPKPKDVLTITLTPK VTCVVVDISKDDPEVQFSWFVDDVEVHTAQTQPREEQFNSTFRSVSELPIM HQDWLNGKEFKCRVNSAAFPAPIEKTISKTKGRPKAPQVYTIPPPKEQMAK DKVSLTCMITDFFPEDITVEWQWNGQPAENYKNTQPIMDTDGSYFVYSKLN VQKSNWEAGNTFTCSVLHEGLHNHHTEKSLSHSPG | 8 |
| Heavy Chain Ab #9 | QVQLQQPGAEVVRPGASVKLSCKASGYSFTSYWIHWLKQGPHQGLEWIG RIDPDDSETHYNQKFKDKALLTVDKSSSTAYMQLRSLTSEDSAVYYCARTN WDAWFAYWGQGTLVTVSAAKTTAPSVYPLAPVCGDTTGSSVTLGCLVKG YFPEPVTLTWNSGSLSSGVHTFPAVLQSDLYTLSSSVTVTSSTWPSQSITC NVAHPASSTKVDKKIHHHHHHHH | 9 |
| Heavy Chain Ab #10 | QVQLQQPGAEVVRPGASVKLSCKASGYSFTSYWIHWLKQGPHQGLEWIG RIDPDDSETHYNQKFKDKALLTVDKSSSTAYMQLRSLTSEDSAVYYCARTN WDAWFAYWGQGTLVTVSAAKTTAPSVYPLAPVCGDTTGSSVTLGCLVKG YFPEPVTLTWNSGSLSSGVHTFPAVLQSDLYTLSSSVTVTSSTWPSQSITC NVAHPASSTKVDKKIEPRGPTIKHHHHHHHH | 10 |
| Heavy Chain Ab #11 | QVQLQQPGAEVVRPGASVKLSCKASGYSFTSYWIHWLKQGPHQGLEWIG RIDPDDSETHYNQKFKDKALLTVDKSSSTAYMQLRSLTSEDSAVYYCARTN WDAWFAYWGQGTLVTVSAAKTTAPSVYPLAPVCGDTTGSSVTLGCLVKG YFPEPVTLTWNSGSLSSGVHTFPAVLQSDLYTLSSSVTVTSSTWPSQSITC NVAHPASSTKVDKKIEPRGPTIKPCPPCKCPAPNLHHHHHHHH | 11 |
| Heavy Chain Ab #12 | QVQLQQPGAEVVRPGASVKLSCKASGYSFTSYWIHWLKQGPHQGLEWIG RIDPDDSETHYNQKFKDKALLTVDKSSSTAYMQLRSLTSEDSAVYYCARTN WDAWFAYWGQGTLVTVSAAKTTAPSVYPLAPVCGDTTGSSVTLGCLVKG YFPEPVTLTWNSGSLSSGVHTFPAVLQSDLYTLSSSVTVTSSTWPSQSITC NVAHPASSTKVDKKIEPRGPTIKPCPPCKCPAPNLLGGPSVFHHHHHHHH | 12 |
| Heavy Chain Ab #13 | QVQLQQPGAEVVRPGASVKLSCKASGYSFTSYWIHWLKQGPHQGLEWIG RIDPDDSETHYNQKFKDKALLTVDKSSSTAYMQLRSLTSEDSAVYYCARTN WDAWFAYWGQGTLVTVSAAKTTAPSVYPLAPVCGDTTGSSVTLGCLVKG YFPEPVTLTWNSGSLSSGVHTFPAVLQSDLYTLSSSVTVTSSTWPSQSITC NVAHPASSTKVDKKIEPRGPTIKPCPPCKCPAPNLLGGPSVFIFPPKIKDV LMISLHHHHHHHH | 13 |
| Heavy Chain Ab #14 | QVQLQQPGAEVVRPGASVKLSCKASGYSFTSYWIHWLKQGPHQGLEWIG RIDPDDSETHYNQKFKDKALLTVDKSSSTAYMQLRSLTSEDSAVYYCARTN WDAWFAYWGQGTLVTVSAAKTTPPSVYPLAPGSAAQTNSMVTLGCLVKG YFPEPVTVTWNSGSLSSGVHTFPAVLQSDLYTLSSSVTVPSSTWPSETVTC NVAHPASSTKVDKKIHHHHHHK | 14 |
| Heavy Chain Ab #15 | QVQLQQPGAEVVRPGASVKLSCKASGYSFTSYWIHWLKQGPHQGLEWIG RIDPDDSETHYNQKFKDKALLTVDKSSSTAYMQLRSLTSEDSAVYYCARTN WDAWFAYWGQGTLVTVSAAKTTPPSVYPLAPGSAAQTNSMVTLGCLVKG YFPEPVTVTWNSGSLSSGVHTFPAVLQSDLYTLSSSVTVPSSTWPSETVTC NVAHPASSTKVDKKIVPRDCGCKPCICTVPEVHHHHHHK | 15 |
| Heavy Chain Ab #16 | QVQLQQPGAEVVRPGASVKLSCKASGYSFTSYWIHWLKQGPHQGLEWIG RIDPDDSETHYNQKFKDKALLTVDKSSSTAYMQLRSLTSEDSAVYYCARTN WDAWFAYWGQGTLVTVSAAKTTPPSVYPLAPGSAAQTNSMVTLGCLVKG YFPEPVTVTWNSGSLSSGVHTFPAVLQSDLYTLSSSVTVPSSTWPSETVTC NVAHPASSTKVDKKIVPRDCGCKPCICTVPEVHHHHHHGSGGK* | 16 |
| Light Chain Abs #1-16 | DIVMTQSPSSLAMSVGQKVTMSCKSSQSLLNSSSQKNYLAWYQQKPGQS PKLLVYFASTRESGVPDRFIGSGSGTDFTLTISSVQAEDLADYFCQQHYRTP WTFGGGTKLEIKRADAAPTVSIFPPSSEQLTSGGASVVCFLNNFYPKDINVK WKIDGSERQNGVLNSWTDQDSKDSTYSMSSTLTLTKDEYERHNSYTCEAT HKTSTSPIVKSFNRNEC | 17 |
| Variable Light Chain | DIVMTQSPSSLAMSVGQKVTMSCKSSQSLLNSSSQKNYLAWYQQKPGQS PKLLVYFASTRESGVPDRFIGSGSGTDFTLTISSVQAEDLADYFCQQHYRTP WTFGGGTKLEIK | 18 |

TABLE 2-continued

SEQUENCE TABLE
Sequences associated with the recombinant antibody of the present invention are outlined below in Table 3.

| Name | Sequence | SEQ ID NO: |
|---|---|---|
| Variable Heavy Chain V1 | QVQLQQPGAEVVRPGASVKLSCKASGYSFTSYWIHWLKQGPHQGLEWIG RIDPDDSETHYNQKFKDKALLTVDKSSSTAYMQLRSLTSEDSAVYYCARTN WDAWFAYWGQGTLVTVSA | 19 |
| Variable Heavy Chain V2 | QVQLQQPGAEVVRPGASVKLSCQTSGYSFTSYWIHWLKQGPHQGLEWIG RIDPDDSETHYNQKFKDKALLTVDKSSSTAYMQLRSLTSEDSAVYYCARTN WDAWFAYWGQGTLVTASA | 20 |
| Variable Heavy Chain V3 | QVQLQQPGAEVVRPGASVKLSCKASGYSFTSYWIHWLKQGPHQGLEWIG RLDPDDSETHYLEKFQGKELLTVDKSSSTAYMQLRSLTSEDSAVYYCARTN WDAWFAYWGQGTLVTVSA | 21 |
| Variable Heavy Chain V4 | QVQLQQPGAEVVRPGASVKLSCQTSGYSFTSYWIHWLKQGPHQGLEWIG RLDPDDSETHYLEKFQGKELLTVDKSSSTAYMQLRSLTSEDSAVYYCARTN WDAWFAYWGQGTLVTASA | 22 |
| LCDR1 (Kabat) | KSSQSLLNSSSQKNYLA | 31 |
| LCDR2 (Kabat) | FASTRES | 32 |
| LCDR3 (Kabat) | QQHYRTPWT | 33 |
| HCDR1 (Kabat) | SYWIH | 34 |
| HCDR2 (Chothia) | DPDDSE | 35 |
| HCDR3 (Kabat) | TNWDAWFAY | 36 |
| HCDR2 Kabat, Variable HC V1 & V2 | RIDPDDSETHYNQKFKD | 37 |
| HCDR2 Kabat, Variable HC V3 & V4 | RLDPDDSETHYLEKFQG | 38 |

REFERENCES

1. Adam, S. S., Key, N. S. & Greenberg, C. S. D-Dimer antigen: Current concepts and future prospects. *Blood* 113, 2878-2887 (2009).
2. Thachil, J., Lippi, G. & Favaloro, E. J. D-Dimer Testing: Laboratory Aspects and Current Issues. *Methods Mol. Biol.* 1646, 91-104 (2017).
3. Weitz, J. I., Fredenburgh, J. C. & Eikelboom, J. W. A Test in Context: D-Dimer. *J. Am. Coll. Cardiol.* 70, 2411-2420 (2017).
4. Riley, R. S., Gilbert, A. R., Dalton, J. B., Pai, S. & McPherson, R. A. Widely used types and clinical applications of D-Dimer assay. *Lab Med.* 47, 90-102 (2016).
5. Goodacre, S., Sampson, F. C., Sutton, A. J., Mason, S. & Morris, F. Variation in the diagnostic performance of D-Dimer for suspected deep vein thrombosis. *QJM* 98, 513-27 (2005).
6. Lippi, G., Ippolito, L., Tondelli, M. T. & Favaloro, E. J. Interference from heterophilic antibodies in D-Dimer assessment. A case report. *Blood Coagul. Fibrinolysis* 25, 277-9 (2014).
7. Robier, C., Edler, E., Klescher, D. & Neubauer, M. False-positive D-Dimer result in a latex-enhanced immunoassay caused by interfering human anti-mouse antibodies. *Clin. Chem. Lab. Med.* 52, e253-e255 (2014).
8. Coco-Martin, J. M., Oberink, J. W., Brunink, F., Van der Velden-de Groot, T. A. & Beuvery, E. C. Instability of a hybridoma cell line in a homogeneous continuous perfusion culture system. *Hybridoma* 11, 653-65 (1992).
9. Castillo, F. J. et al. Hybridoma stability. *Dev. Biol. Stand.* 83, 55-64 (1994).
10. Gupta, S. K. & Shukla, P. Glycosylation control technologies for recombinant therapeutic proteins. *Appl. Microbiol. Biotechnol.* 102, 10457-10468 (2018).
11. Holvoet, P., Lijnen, H. R. & Collen, D. A monoclonal antibody preventing binding of tissue-type plasminogen activator to fibrin: useful to monitor fibrinogen breakdown during t-PA infusion. *Blood* 67, 1482-7 (1986).
12. P Holveot, J M Stassen, Y Hashimoto, D Spriggs, P Devos, D. C. Binding properties of monoclonal antibodies against human fragment D-dim . . . pdf. *Thombosis Haemost.* 61, 307-313 (1989).

The invention claimed is:

1. An anti-D-dimer recombinant antibody that specifically binds to fibrin degradation products and fibrinogen degradation products, wherein the fibrin degradation products and the fibrinogen degradation products include D-Dimer, fragment DD and fragment D, but the recombinant antibody does not bind to either fragment E and fibrinogen, wherein fragment E is a fibrin degradation product or a fibrinogen degradation product, and wherein the anti-D-dimer recombinant antibody comprises:

a light chain variable region comprising the amino acid sequence of SEQ ID NO: 31 (L-CDR1); the amino acid sequence of SEQ ID NO: 32 (L-CDR2); and the amino acid sequence of SEQ ID NO: 33 (L-CDR3); and a heavy chain variable region comprising the amino acid sequence of SEQ ID NO: 34 (H-CDR1); an amino acid sequence selected from the group consisting of SEQ ID NO: 35, SEQ ID NO: 37, and SEQ ID NO: 38 (H-CDR2); and the amino acid sequence of SEQ ID NO: 36 (H-CDR3).

2. The recombinant antibody according to claim 1, wherein said light chain comprises the amino acid sequence of SEQ ID NO: 18.

3. The recombinant antibody according to claim 1, wherein said heavy chain comprises the amino acid sequence of SEQ ID NO: 19, or SEQ ID NO: 20, or SEQ ID NO: 21 or SEQ ID NO: 22.

4. The recombinant antibody according to claim 1, comprising:

a light chain variable region comprising an amino acid sequence at least about 90%, 91%, 92%, 93%, 94%, 95%, 96%, 97%, 98%, or about 99% identical to SEQ ID NO: 18, and a heavy chain variable region comprising an amino acid sequence at least about 90%, 91%, 92%, 93%, 94%, 95%, 96%, 97%, 98%, or about 99% identical to a sequence selected from the group consisting of SEQ ID NOs: 19, 20, 21, and 22.

5. The recombinant antibody according to claim 1, comprising:

a light chain variable region comprising the amino acid sequence of SEQ ID NO: 18, and a heavy chain variable region comprising an amino acid sequence selected from the group consisting of SEQ ID NOs: 19, 20, 21, and 22.

6. The recombinant antibody according to claim 1, comprising:

a light chain variable region comprising the amino acid sequence of SEQ ID NO: 18, and a heavy chain variable region comprising an amino acid sequence selected from the group consisting of SEQ ID NOs: 19 and 20.

7. The recombinant antibody according to claim 1, further comprising an affinity tag.

8. The recombinant antibody according to claim 7, wherein the amino acid sequence of the affinity tag is selected from the group consisting of SEQ ID NO: 23, SEQ ID NO: 24, or SEQ ID NO: 25.

9. The recombinant antibody according to claim 1, wherein the light chain of said recombinant antibody comprises the amino acid sequence of SEQ ID NO: 17.

10. The recombinant antibody according claim 1, wherein the heavy chain of said recombinant antibody comprises the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, or SEQ ID NO: 16.

11. The recombinant antibody according to claim 1, wherein the light chain of said recombinant antibody comprises the amino acid sequence of SEQ ID NO: 17 and the heavy chain of said recombinant antibody comprises the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, or SEQ ID NO:16.

12. The recombinant antibody according to claim 1, wherein the recombinant antibody comprises the amino acid sequence of SEQ ID NO: 17 and the amino acid sequence of SEQ ID NO: 12.

* * * * *

SEQUENCE LISTING

<160> NUMBER OF SEQ ID NOS: 38

<210> SEQ ID NO 1
<211> LENGTH: 441
<212> TYPE: PRT
<213> ORGANISM: Artificial Sequence
<220> FEATURE:
<223> OTHER INFORMATION: Synthetic peptide

<400> SEQUENCE: 1

Gln Val Gln Leu Gln Gln Pro Gly Ala Glu Val Val Arg Pro Gly Ala
1 5 10 15

Ser Val Lys Leu Ser Cys Gln Thr Ser Gly Tyr Ser Phe Thr Ser Tyr
20 25 30

Trp Ile His Trp Leu Lys Gln Gly Pro His Gln Gly Leu Glu Trp Ile
35 40 45

Gly Arg Leu Asp Pro Asp Asp Ser Glu Thr His Tyr Leu Glu Lys Phe
50 55 60

Gln Gly Lys Glu Leu Leu Thr Val Asp Lys Ser Ser Ser Thr Ala Tyr
65 70 75 80

Met Gln Leu Arg Ser Leu Thr Ser Glu Asp Ser Ala Val Tyr Tyr Cys
85 90 95

Ala Arg Thr Asn Trp Asp Ala Trp Phe Ala Tyr Trp Gly Gln Gly Thr
100 105 110

Leu Val Thr Ala Ser Ala Ala Lys Thr Thr Pro Pro Ser Val Tyr Pro
115 120 125

Leu Ala Pro Gly Ser Ala Ala Gln Thr Asn Ser Met Val Thr Leu Gly
130 135 140

Cys Leu Val Lys Gly Tyr Phe Pro Glu Pro Val Thr Val Thr Trp Asn
145 150 155 160

Ser Gly Ser Leu Ser Ser Gly Val His Thr Phe Pro Ala Val Leu Gln
165 170 175

Ser Asp Leu Tyr Thr Leu Ser Ser Ser Val Thr Val Pro Ser Ser Thr
180 185 190

Trp Pro Ser Gln Thr Val Thr Cys Asn Val Ala His Pro Ala Ser Ser
195 200 205

Thr Lys Val Asp Lys Lys Ile Val Pro Arg Asp Cys Gly Cys Lys Pro
210 215 220

Cys Ile Cys Thr Val Pro Glu Val Ser Ser Val Phe Ile Phe Pro Pro
225 230 235 240

Lys Pro Lys Asp Val Leu Thr Ile Thr Leu Thr Pro Lys Val Thr Cys
245 250 255

Val Val Val Asp Ile Ser Lys Asp Asp Pro Glu Val Gln Phe Ser Trp
260 265 270

Phe Val Asp Asp Val Glu Val His Thr Ala Gln Thr Gln Pro Arg Glu
275 280 285

Glu Gln Phe Asn Ser Thr Phe Arg Ser Val Ser Glu Leu Pro Ile Met
290 295 300

His Gln Asp Trp Leu Asn Gly Lys Glu Phe Lys Cys Arg Val Asn Ser
305 310 315 320

Ala Ala Phe Pro Ala Pro Ile Glu Lys Thr Ile Ser Lys Thr Lys Gly
325 330 335

Arg Pro Lys Ala Pro Gln Val Tyr Thr Ile Pro Pro Pro Lys Glu Gln
340 345 350

Met Ala Lys Asp Lys Val Ser Leu Thr Cys Met Ile Thr Asp Phe Phe

```
        355                 360                 365

Pro Glu Asp Ile Thr Val Glu Trp Gln Trp Asn Gly Gln Pro Ala Glu
    370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
            420                 425                 430

Glu Lys Ser Leu Ser His Ser Pro Gly
        435                 440


<210> SEQ ID NO 2
<211> LENGTH: 441
<212> TYPE: PRT
<213> ORGANISM: Artificial Sequence
<220> FEATURE:
<223> OTHER INFORMATION: Synthetic peptide

<400> SEQUENCE: 2

Gln Val Gln Leu Gln Gln Pro Gly Ala Glu Val Val Arg Pro Gly Ala
1               5                   10                  15

Ser Val Lys Leu Ser Cys Gln Thr Ser Gly Tyr Ser Phe Thr Ser Tyr
            20                  25                  30

Trp Ile His Trp Leu Lys Gln Gly Pro His Gln Gly Leu Glu Trp Ile
        35                  40                  45

Gly Arg Leu Asp Pro Asp Asp Ser Glu Thr His Tyr Leu Glu Lys Phe
    50                  55                  60

Gln Gly Lys Glu Leu Leu Thr Val Asp Lys Ser Ser Ser Thr Ala Tyr
65                  70                  75                  80

Met Gln Leu Arg Ser Leu Thr Ser Glu Asp Ser Ala Val Tyr Tyr Cys
                85                  90                  95

Ala Arg Thr Asn Trp Asp Ala Trp Phe Ala Tyr Trp Gly Gln Gly Thr
            100                 105                 110

Leu Val Thr Ala Ser Ala Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Glu Thr Val Thr Cys Asn Val Ala His Pro Ala Ser Ser
        195                 200                 205

Thr Lys Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Gln Pro Arg Glu
```

```
        275                 280                 285

Glu Gln Phe Asn Ser Thr Phe Arg Ser Val Ser Glu Leu Pro Ile Met
    290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Pro Lys Glu Gln
            340                 345                 350

Met Ala Lys Asp Lys Val Ser Leu Thr Cys Met Ile Thr Asp Phe Phe
        355                 360                 365

Pro Glu Asp Ile Thr Val Glu Trp Gln Trp Asn Gly Gln Pro Ala Glu
    370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
            420                 425                 430

Glu Lys Ser Leu Ser His Ser Pro Gly
        435                 440


<210> SEQ ID NO 3
<211> LENGTH: 441
<212> TYPE: PRT
<213> ORGANISM: Artificial Sequence
<220> FEATURE:
<223> OTHER INFORMATION: Synthetic peptide

<400> SEQUENCE: 3

Gln Val Gln Leu Gln Gln Pro Gly Ala Glu Val Val Arg Pro Gly Ala
1               5                   10                  15

Ser Val Lys Leu Ser Cys Gln Thr Ser Gly Tyr Ser Phe Thr Ser Tyr
            20                  25                  30

Trp Ile His Trp Leu Lys Gln Gly Pro His Gln Gly Leu Glu Trp Ile
        35                  40                  45

Gly Arg Leu Asp Pro Asp Asp Ser Glu Thr His Tyr Leu Glu Lys Phe
    50                  55                  60

Gln Gly Lys Glu Leu Leu Thr Val Asp Lys Ser Ser Ser Thr Ala Tyr
65                  70                  75                  80

Met Gln Leu Arg Ser Leu Thr Ser Glu Asp Ser Ala Val Tyr Tyr Cys
                85                  90                  95

Ala Arg Thr Asn Trp Asp Ala Trp Phe Ala Tyr Trp Gly Gln Gly Thr
            100                 105                 110

Leu Val Thr Ala Ser Ala Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Glu Thr Val Thr Cys Asn Val Ala His Pro Ala Ser Ser
```

```
        195                 200                 205

Thr Lys Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Gln Pro Arg Glu
        275                 280                 285

Glu Gln Phe Asn Ser Thr Phe Arg Ser Val Ser Glu Leu Pro Ile Met
    290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Pro Lys Glu Gln
            340                 345                 350

Met Ala Lys Asp Lys Val Ser Leu Thr Cys Met Ile Thr Asp Phe Phe
        355                 360                 365

Pro Glu Asp Ile Thr Val Glu Trp Gln Trp Asn Gly Gln Pro Ala Glu
    370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
            420                 425                 430

Glu Lys Ser Leu Ser His Ser Pro Gly
        435                 440


<210> SEQ ID NO 4
<211> LENGTH: 447
<212> TYPE: PRT
<213> ORGANISM: Artificial Sequence
<220> FEATURE:
<223> OTHER INFORMATION: Synthetic peptide

<400> SEQUENCE: 4

Gln Val Gln Leu Gln Gln Pro Gly Ala Glu Val Val Arg Pro Gly Ala
1               5                   10                  15

Ser Val Lys Leu Ser Cys Lys Ala Ser Gly Tyr Ser Phe Thr Ser Tyr
            20                  25                  30

Trp Ile His Trp Leu Lys Gln Gly Pro His Gln Gly Leu Glu Trp Ile
        35                  40                  45

Gly Arg Leu Asp Pro Asp Asp Ser Glu Thr His Tyr Leu Glu Lys Phe
    50                  55                  60

Gln Gly Lys Glu Leu Leu Thr Val Asp Lys Ser Ser Ser Thr Ala Tyr
65                  70                  75                  80

Met Gln Leu Arg Ser Leu Thr Ser Glu Asp Ser Ala Val Tyr Tyr Cys
                85                  90                  95

Ala Arg Thr Asn Trp Asp Ala Trp Phe Ala Tyr Trp Gly Gln Gly Thr
            100                 105                 110

Leu Val Thr Val Ser Ala Ala Lys Thr Thr Ala Pro Ser Val Tyr Pro
```

```
        115                 120                 125

Leu Ala Pro Val Cys Gly Asp Thr Thr Gly Ser Ser Val Thr Leu Gly
    130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

Thr Lys Val Asp Lys Lys Ile Glu Pro Arg Gly Pro Thr Ile Lys Pro
    210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Val Asp Val Ser Glu Asp Asp Pro
            260                 265                 270

Asp Val Gln Ile Ser Trp Phe Val Asn Asn Val Glu Val His Thr Ala
        275                 280                 285

Gln Thr Gln Thr His Arg Glu Asp Tyr Asn Ser Thr Leu Arg Val Val
    290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
            340                 345                 350

Pro Pro Pro Glu Glu Glu Met Thr Lys Lys Gln Val Thr Leu Thr Cys
        355                 360                 365

Met Val Thr Asp Phe Met Pro Glu Asp Ile Tyr Val Glu Trp Thr Asn
    370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
            420                 425                 430

Leu His Asn His His Thr Thr Lys Ser Phe Ser Arg Thr Pro Gly
        435                 440                 445


<210> SEQ ID NO 5
<211> LENGTH: 447
<212> TYPE: PRT
<213> ORGANISM: Artificial Sequence
<220> FEATURE:
<223> OTHER INFORMATION: Synthetic peptide

<400> SEQUENCE: 5

Gln Val Gln Leu Gln Gln Pro Gly Ala Glu Val Val Arg Pro Gly Ala
1               5                   10                  15

Ser Val Lys Leu Ser Cys Lys Ala Ser Gly Tyr Ser Phe Thr Ser Tyr
            20                  25                  30

Trp Ile His Trp Leu Lys Gln Gly Pro His Gln Gly Leu Glu Trp Ile
```

```
        35                  40                  45

Gly Arg Ile Asp Pro Asp Asp Ser Glu Thr His Tyr Asn Gln Lys Phe
    50                  55                  60

Lys Asp Lys Ala Leu Leu Thr Val Asp Lys Ser Ser Ser Thr Ala Tyr
65                  70                  75                  80

Met Gln Leu Arg Ser Leu Thr Ser Glu Asp Ser Ala Val Tyr Tyr Cys
                85                  90                  95

Ala Arg Thr Asn Trp Asp Ala Trp Phe Ala Tyr Trp Gly Gln Gly Thr
            100                 105                 110

Leu Val Thr Val Ser Ala Ala Lys Thr Thr Ala Pro Ser Val Tyr Pro
        115                 120                 125

Leu Ala Pro Val Cys Gly Asp Thr Thr Gly Ser Ser Val Thr Leu Gly
    130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

Thr Lys Val Asp Lys Lys Ile Glu Pro Arg Gly Pro Thr Ile Lys Pro
    210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Val Asp Val Ser Glu Asp Asp Pro
            260                 265                 270

Asp Val Gln Ile Ser Trp Phe Val Asn Asn Val Glu Val His Thr Ala
        275                 280                 285

Gln Thr Gln Thr His Arg Glu Asp Tyr Asn Ser Thr Leu Arg Val Val
    290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
            340                 345                 350

Pro Pro Pro Glu Glu Glu Met Thr Lys Lys Gln Val Thr Leu Thr Cys
        355                 360                 365

Met Val Thr Asp Phe Met Pro Glu Asp Ile Tyr Val Glu Trp Thr Asn
    370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
            420                 425                 430

Leu His Asn His His Thr Thr Lys Ser Phe Ser Arg Thr Pro Gly
        435                 440                 445
```

<210> SEQ ID NO 6

```
<211> LENGTH: 441
<212> TYPE: PRT
<213> ORGANISM: Artificial Sequence
<220> FEATURE:
<223> OTHER INFORMATION: Synthetic peptide

<400> SEQUENCE: 6

Gln Val Gln Leu Gln Gln Pro Gly Ala Glu Val Val Arg Pro Gly Ala
1               5                   10                  15

Ser Val Lys Leu Ser Cys Lys Ala Ser Gly Tyr Ser Phe Thr Ser Tyr
            20                  25                  30

Trp Ile His Trp Leu Lys Gln Gly Pro His Gln Gly Leu Glu Trp Ile
        35                  40                  45

Gly Arg Ile Asp Pro Asp Asp Ser Glu Thr His Tyr Asn Gln Lys Phe
    50                  55                  60

Lys Asp Lys Ala Leu Leu Thr Val Asp Lys Ser Ser Ser Thr Ala Tyr
65                  70                  75                  80

Met Gln Leu Arg Ser Leu Thr Ser Glu Asp Ser Ala Val Tyr Tyr Cys
                85                  90                  95

Ala Arg Thr Asn Trp Asp Ala Trp Phe Ala Tyr Trp Gly Gln Gly Thr
            100                 105                 110

Leu Val Thr Val Ser Ala Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Glu Thr Val Thr Cys Asn Val Ala His Pro Ala Ser Ser
        195                 200                 205

Thr Lys Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Gln Pro Arg Glu
        275                 280                 285

Glu Gln Phe Asn Ser Thr Phe Arg Ser Val Ser Glu Leu Pro Ile Met
    290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Pro Lys Glu Gln
            340                 345                 350

Met Ala Lys Asp Lys Val Ser Leu Thr Cys Met Ile Thr Asp Phe Phe
        355                 360                 365

Pro Glu Asp Ile Thr Val Glu Trp Gln Trp Asn Gly Gln Pro Ala Glu
    370                 375                 380
```

```
Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
            420                 425                 430

Glu Lys Ser Leu Ser His Ser Pro Gly
        435                 440


<210> SEQ ID NO 7
<211> LENGTH: 447
<212> TYPE: PRT
<213> ORGANISM: Artificial Sequence
<220> FEATURE:
<223> OTHER INFORMATION: Synthetic peptide

<400> SEQUENCE: 7

Gln Val Gln Leu Gln Gln Pro Gly Ala Glu Val Val Arg Pro Gly Ala
1               5                   10                  15

Ser Val Lys Leu Ser Cys Gln Thr Ser Gly Tyr Ser Phe Thr Ser Tyr
            20                  25                  30

Trp Ile His Trp Leu Lys Gln Gly Pro His Gln Gly Leu Glu Trp Ile
        35                  40                  45

Gly Arg Ile Asp Pro Asp Asp Ser Glu Thr His Tyr Asn Gln Lys Phe
    50                  55                  60

Lys Asp Lys Ala Leu Leu Thr Val Asp Lys Ser Ser Ser Thr Ala Tyr
65                  70                  75                  80

Met Gln Leu Arg Ser Leu Thr Ser Glu Asp Ser Ala Val Tyr Tyr Cys
                85                  90                  95

Ala Arg Thr Asn Trp Asp Ala Trp Phe Ala Tyr Trp Gly Gln Gly Thr
            100                 105                 110

Leu Val Thr Ala Ser Ala Ala Lys Thr Thr Ala Pro Ser Val Tyr Pro
        115                 120                 125

Leu Ala Pro Val Cys Gly Asp Thr Thr Gly Ser Ser Val Thr Leu Gly
    130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

Thr Lys Val Asp Lys Lys Ile Glu Pro Arg Gly Pro Thr Ile Lys Pro
    210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Val Asp Val Ser Glu Asp Asp Pro
            260                 265                 270

Asp Val Gln Ile Ser Trp Phe Val Asn Asn Val Glu Val His Thr Ala
        275                 280                 285

Gln Thr Gln Thr His Arg Glu Asp Tyr Asn Ser Thr Leu Arg Val Val
    290                 295                 300
```

```
Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
            340                 345                 350

Pro Pro Pro Glu Glu Glu Met Thr Lys Lys Gln Val Thr Leu Thr Cys
        355                 360                 365

Met Val Thr Asp Phe Met Pro Glu Asp Ile Tyr Val Glu Trp Thr Asn
    370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
            420                 425                 430

Leu His Asn His His Thr Thr Lys Ser Phe Ser Arg Thr Pro Gly
        435                 440                 445


<210> SEQ ID NO 8
<211> LENGTH: 441
<212> TYPE: PRT
<213> ORGANISM: Artificial Sequence
<220> FEATURE:
<223> OTHER INFORMATION: Synthetic peptide

<400> SEQUENCE: 8

Gln Val Gln Leu Gln Gln Pro Gly Ala Glu Val Val Arg Pro Gly Ala
1               5                   10                  15

Ser Val Lys Leu Ser Cys Gln Thr Ser Gly Tyr Ser Phe Thr Ser Tyr
            20                  25                  30

Trp Ile His Trp Leu Lys Gln Gly Pro His Gln Gly Leu Glu Trp Ile
        35                  40                  45

Gly Arg Ile Asp Pro Asp Asp Ser Glu Thr His Tyr Asn Gln Lys Phe
    50                  55                  60

Lys Asp Lys Ala Leu Leu Thr Val Asp Lys Ser Ser Ser Thr Ala Tyr
65                  70                  75                  80

Met Gln Leu Arg Ser Leu Thr Ser Glu Asp Ser Ala Val Tyr Tyr Cys
                85                  90                  95

Ala Arg Thr Asn Trp Asp Ala Trp Phe Ala Tyr Trp Gly Gln Gly Thr
            100                 105                 110

Leu Val Thr Ala Ser Ala Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Glu Thr Val Thr Cys Asn Val Ala His Pro Ala Ser Ser
        195                 200                 205

Thr Lys Val Asp Lys Lys Ile Val Pro Arg Asp Cys Gly Cys Lys Pro
    210                 215                 220
```

```
Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Gln Pro Arg Glu
        275                 280                 285

Glu Gln Phe Asn Ser Thr Phe Arg Ser Val Ser Glu Leu Pro Ile Met
    290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Pro Lys Glu Gln
            340                 345                 350

Met Ala Lys Asp Lys Val Ser Leu Thr Cys Met Ile Thr Asp Phe Phe
        355                 360                 365

Pro Glu Asp Ile Thr Val Glu Trp Gln Trp Asn Gly Gln Pro Ala Glu
    370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
            420                 425                 430

Glu Lys Ser Leu Ser His Ser Pro Gly
        435                 440


<210> SEQ ID NO 9
<211> LENGTH: 223
<212> TYPE: PRT
<213> ORGANISM: Artificial Sequence
<220> FEATURE:
<223> OTHER INFORMATION: Synthetic peptide

<400> SEQUENCE: 9

Gln Val Gln Leu Gln Gln Pro Gly Ala Glu Val Val Arg Pro Gly Ala
1               5                   10                  15

Ser Val Lys Leu Ser Cys Lys Ala Ser Gly Tyr Ser Phe Thr Ser Tyr
            20                  25                  30

Trp Ile His Trp Leu Lys Gln Gly Pro His Gln Gly Leu Glu Trp Ile
        35                  40                  45

Gly Arg Ile Asp Pro Asp Asp Ser Glu Thr His Tyr Asn Gln Lys Phe
    50                  55                  60

Lys Asp Lys Ala Leu Leu Thr Val Asp Lys Ser Ser Ser Thr Ala Tyr
65                  70                  75                  80

Met Gln Leu Arg Ser Leu Thr Ser Glu Asp Ser Ala Val Tyr Tyr Cys
                85                  90                  95

Ala Arg Thr Asn Trp Asp Ala Trp Phe Ala Tyr Trp Gly Gln Gly Thr
            100                 105                 110

Leu Val Thr Val Ser Ala Ala Lys Thr Thr Ala Pro Ser Val Tyr Pro
        115                 120                 125

Leu Ala Pro Val Cys Gly Asp Thr Thr Gly Ser Ser Val Thr Leu Gly
    130                 135                 140
```

```
Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

Thr Lys Val Asp Lys Lys Ile His His His His His His His His
    210                 215                 220


<210> SEQ ID NO 10
<211> LENGTH: 231
<212> TYPE: PRT
<213> ORGANISM: Artificial Sequence
<220> FEATURE:
<223> OTHER INFORMATION: Synthetic peptide

<400> SEQUENCE: 10

Gln Val Gln Leu Gln Gln Pro Gly Ala Glu Val Val Arg Pro Gly Ala
1               5                   10                  15

Ser Val Lys Leu Ser Cys Lys Ala Ser Gly Tyr Ser Phe Thr Ser Tyr
            20                  25                  30

Trp Ile His Trp Leu Lys Gln Gly Pro His Gln Gly Leu Glu Trp Ile
        35                  40                  45

Gly Arg Ile Asp Pro Asp Asp Ser Glu Thr His Tyr Asn Gln Lys Phe
    50                  55                  60

Lys Asp Lys Ala Leu Leu Thr Val Asp Lys Ser Ser Ser Thr Ala Tyr
65                  70                  75                  80

Met Gln Leu Arg Ser Leu Thr Ser Glu Asp Ser Ala Val Tyr Tyr Cys
                85                  90                  95

Ala Arg Thr Asn Trp Asp Ala Trp Phe Ala Tyr Trp Gly Gln Gly Thr
            100                 105                 110

Leu Val Thr Val Ser Ala Ala Lys Thr Thr Ala Pro Ser Val Tyr Pro
        115                 120                 125

Leu Ala Pro Val Cys Gly Asp Thr Thr Gly Ser Ser Val Thr Leu Gly
    130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

Thr Lys Val Asp Lys Lys Ile Glu Pro Arg Gly Pro Thr Ile Lys His
    210                 215                 220

His His His His His His His
225                 230


<210> SEQ ID NO 11
<211> LENGTH: 243
<212> TYPE: PRT
<213> ORGANISM: Artificial Sequence
<220> FEATURE:
<223> OTHER INFORMATION: Synthetic peptide
```

<400> SEQUENCE: 11

```
Gln Val Gln Leu Gln Gln Pro Gly Ala Glu Val Val Arg Pro Gly Ala
1               5                   10                  15

Ser Val Lys Leu Ser Cys Lys Ala Ser Gly Tyr Ser Phe Thr Ser Tyr
            20                  25                  30

Trp Ile His Trp Leu Lys Gln Gly Pro His Gln Gly Leu Glu Trp Ile
        35                  40                  45

Gly Arg Ile Asp Pro Asp Asp Ser Glu Thr His Tyr Asn Gln Lys Phe
    50                  55                  60

Lys Asp Lys Ala Leu Leu Thr Val Asp Lys Ser Ser Ser Thr Ala Tyr
65                  70                  75                  80

Met Gln Leu Arg Ser Leu Thr Ser Glu Asp Ser Ala Val Tyr Tyr Cys
                85                  90                  95

Ala Arg Thr Asn Trp Asp Ala Trp Phe Ala Tyr Trp Gly Gln Gly Thr
            100                 105                 110

Leu Val Thr Val Ser Ala Ala Lys Thr Thr Ala Pro Ser Val Tyr Pro
        115                 120                 125

Leu Ala Pro Val Cys Gly Asp Thr Thr Gly Ser Ser Val Thr Leu Gly
    130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

Thr Lys Val Asp Lys Lys Ile Glu Pro Arg Gly Pro Thr Ile Lys Pro
    210                 215                 220

Cys Pro Pro Cys Lys Cys Pro Ala Pro Asn Leu His His His His His
225                 230                 235                 240

His His His
```

<210> SEQ ID NO 12
<211> LENGTH: 250
<212> TYPE: PRT
<213> ORGANISM: Artificial Sequence
<220> FEATURE:
<223> OTHER INFORMATION: Synthetic peptide

<400> SEQUENCE: 12

```
Gln Val Gln Leu Gln Gln Pro Gly Ala Glu Val Val Arg Pro Gly Ala
1               5                   10                  15

Ser Val Lys Leu Ser Cys Lys Ala Ser Gly Tyr Ser Phe Thr Ser Tyr
            20                  25                  30

Trp Ile His Trp Leu Lys Gln Gly Pro His Gln Gly Leu Glu Trp Ile
        35                  40                  45

Gly Arg Ile Asp Pro Asp Asp Ser Glu Thr His Tyr Asn Gln Lys Phe
    50                  55                  60

Lys Asp Lys Ala Leu Leu Thr Val Asp Lys Ser Ser Ser Thr Ala Tyr
65                  70                  75                  80

Met Gln Leu Arg Ser Leu Thr Ser Glu Asp Ser Ala Val Tyr Tyr Cys
                85                  90                  95

Ala Arg Thr Asn Trp Asp Ala Trp Phe Ala Tyr Trp Gly Gln Gly Thr
            100                 105                 110
```

```
Leu Val Thr Val Ser Ala Ala Lys Thr Thr Ala Pro Ser Val Tyr Pro
        115                 120                 125

Leu Ala Pro Val Cys Gly Asp Thr Thr Gly Ser Ser Val Thr Leu Gly
    130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

Thr Lys Val Asp Lys Lys Ile Glu Pro Arg Gly Pro Thr Ile Lys Pro
    210                 215                 220

Cys Pro Pro Cys Lys Cys Pro Ala Pro Asn Leu Leu Gly Gly Pro Ser
225                 230                 235                 240

Val Phe His His His His His His His His
                245                 250


<210> SEQ ID NO 13
<211> LENGTH: 264
<212> TYPE: PRT
<213> ORGANISM: Artificial Sequence
<220> FEATURE:
<223> OTHER INFORMATION: Synthetic peptide

<400> SEQUENCE: 13

Gln Val Gln Leu Gln Gln Pro Gly Ala Glu Val Val Arg Pro Gly Ala
1               5                   10                  15

Ser Val Lys Leu Ser Cys Lys Ala Ser Gly Tyr Ser Phe Thr Ser Tyr
            20                  25                  30

Trp Ile His Trp Leu Lys Gln Gly Pro His Gln Gly Leu Glu Trp Ile
        35                  40                  45

Gly Arg Ile Asp Pro Asp Asp Ser Glu Thr His Tyr Asn Gln Lys Phe
    50                  55                  60

Lys Asp Lys Ala Leu Leu Thr Val Asp Lys Ser Ser Ser Thr Ala Tyr
65                  70                  75                  80

Met Gln Leu Arg Ser Leu Thr Ser Glu Asp Ser Ala Val Tyr Tyr Cys
                85                  90                  95

Ala Arg Thr Asn Trp Asp Ala Trp Phe Ala Tyr Trp Gly Gln Gly Thr
            100                 105                 110

Leu Val Thr Val Ser Ala Ala Lys Thr Thr Ala Pro Ser Val Tyr Pro
        115                 120                 125

Leu Ala Pro Val Cys Gly Asp Thr Thr Gly Ser Ser Val Thr Leu Gly
    130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

Thr Lys Val Asp Lys Lys Ile Glu Pro Arg Gly Pro Thr Ile Lys Pro
    210                 215                 220
```

```
Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                245                 250                 255

His His His His His His His His
            260


<210> SEQ ID NO 14
<211> LENGTH: 222
<212> TYPE: PRT
<213> ORGANISM: Artificial Sequence
<220> FEATURE:
<223> OTHER INFORMATION: Synthetic peptide

<400> SEQUENCE: 14

Gln Val Gln Leu Gln Gln Pro Gly Ala Glu Val Val Arg Pro Gly Ala
1               5                   10                  15

Ser Val Lys Leu Ser Cys Lys Ala Ser Gly Tyr Ser Phe Thr Ser Tyr
            20                  25                  30

Trp Ile His Trp Leu Lys Gln Gly Pro His Gln Gly Leu Glu Trp Ile
        35                  40                  45

Gly Arg Ile Asp Pro Asp Asp Ser Glu Thr His Tyr Asn Gln Lys Phe
    50                  55                  60

Lys Asp Lys Ala Leu Leu Thr Val Asp Lys Ser Ser Ser Thr Ala Tyr
65                  70                  75                  80

Met Gln Leu Arg Ser Leu Thr Ser Glu Asp Ser Ala Val Tyr Tyr Cys
                85                  90                  95

Ala Arg Thr Asn Trp Asp Ala Trp Phe Ala Tyr Trp Gly Gln Gly Thr
            100                 105                 110

Leu Val Thr Val Ser Ala Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Glu Thr Val Thr Cys Asn Val Ala His Pro Ala Ser Ser
        195                 200                 205

Thr Lys Val Asp Lys Lys Ile His His His His His His Lys
    210                 215                 220


<210> SEQ ID NO 15
<211> LENGTH: 239
<212> TYPE: PRT
<213> ORGANISM: Artificial Sequence
<220> FEATURE:
<223> OTHER INFORMATION: Synthetic peptide

<400> SEQUENCE: 15

Gln Val Gln Leu Gln Gln Pro Gly Ala Glu Val Val Arg Pro Gly Ala
1               5                   10                  15

Ser Val Lys Leu Ser Cys Lys Ala Ser Gly Tyr Ser Phe Thr Ser Tyr
            20                  25                  30

Trp Ile His Trp Leu Lys Gln Gly Pro His Gln Gly Leu Glu Trp Ile
```

```
        35                  40                  45

Gly Arg Ile Asp Pro Asp Asp Ser Glu Thr His Tyr Asn Gln Lys Phe
    50                  55                  60

Lys Asp Lys Ala Leu Leu Thr Val Asp Lys Ser Ser Ser Thr Ala Tyr
65                  70                  75                  80

Met Gln Leu Arg Ser Leu Thr Ser Glu Asp Ser Ala Val Tyr Tyr Cys
                85                  90                  95

Ala Arg Thr Asn Trp Asp Ala Trp Phe Ala Tyr Trp Gly Gln Gly Thr
            100                 105                 110

Leu Val Thr Val Ser Ala Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Glu Thr Val Thr Cys Asn Val Ala His Pro Ala Ser Ser
        195                 200                 205

Thr Lys Val Asp Lys Lys Ile Val Pro Arg Asp Cys Gly Cys Lys Pro
    210                 215                 220

Cys Ile Cys Thr Val Pro Glu Val His His His His His His Lys
225                 230                 235


<210> SEQ ID NO 16
<211> LENGTH: 243
<212> TYPE: PRT
<213> ORGANISM: Artificial Sequence
<220> FEATURE:
<223> OTHER INFORMATION: Synthetic peptide

<400> SEQUENCE: 16

Gln Val Gln Leu Gln Gln Pro Gly Ala Glu Val Val Arg Pro Gly Ala
1               5                   10                  15

Ser Val Lys Leu Ser Cys Lys Ala Ser Gly Tyr Ser Phe Thr Ser Tyr
            20                  25                  30

Trp Ile His Trp Leu Lys Gln Gly Pro His Gln Gly Leu Glu Trp Ile
        35                  40                  45

Gly Arg Ile Asp Pro Asp Asp Ser Glu Thr His Tyr Asn Gln Lys Phe
    50                  55                  60

Lys Asp Lys Ala Leu Leu Thr Val Asp Lys Ser Ser Ser Thr Ala Tyr
65                  70                  75                  80

Met Gln Leu Arg Ser Leu Thr Ser Glu Asp Ser Ala Val Tyr Tyr Cys
                85                  90                  95

Ala Arg Thr Asn Trp Asp Ala Trp Phe Ala Tyr Trp Gly Gln Gly Thr
            100                 105                 110

Leu Val Thr Val Ser Ala Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
```

```
                165                 170                 175

Ser Asp Leu Tyr Thr Leu Ser Ser Ser Val Thr Val Pro Ser Ser Thr
            180                 185                 190

Trp Pro Ser Glu Thr Val Thr Cys Asn Val Ala His Pro Ala Ser Ser
        195                 200                 205

Thr Lys Val Asp Lys Lys Ile Val Pro Arg Asp Cys Gly Cys Lys Pro
    210                 215                 220

Cys Ile Cys Thr Val Pro Glu Val His His His His His His Gly Ser
225                 230                 235                 240

Gly Gly Lys
```

<210> SEQ ID NO 17
<211> LENGTH: 220
<212> TYPE: PRT
<213> ORGANISM: Artificial Sequence
<220> FEATURE:
<223> OTHER INFORMATION: Synthetic peptide

<400> SEQUENCE: 17

```
Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ser Ser Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Arg Thr Pro Trp Thr Phe Gly Gly Gly Thr Lys Leu Glu Ile
            100                 105                 110

Lys Arg Ala Asp Ala Ala Pro Thr Val Ser Ile Phe Pro Pro Ser Ser
        115                 120                 125

Glu Gln Leu Thr Ser Gly Gly Ala Ser Val Val Cys Phe Leu Asn Asn
    130                 135                 140

Phe Tyr Pro Lys Asp Ile Asn Val Lys Trp Lys Ile Asp Gly Ser Glu
145                 150                 155                 160

Arg Gln Asn Gly Val Leu Asn Ser Trp Thr Asp Gln Asp Ser Lys Asp
                165                 170                 175

Ser Thr Tyr Ser Met Ser Ser Thr Leu Thr Leu Thr Lys Asp Glu Tyr
            180                 185                 190

Glu Arg His Asn Ser Tyr Thr Cys Glu Ala Thr His Lys Thr Ser Thr
        195                 200                 205

Ser Pro Ile Val Lys Ser Phe Asn Arg Asn Glu Cys
    210                 215                 220
```

<210> SEQ ID NO 18
<211> LENGTH: 113
<212> TYPE: PRT
<213> ORGANISM: Artificial Sequence
<220> FEATURE:
<223> OTHER INFORMATION: Synthetic peptide

<400> SEQUENCE: 18

```
Asp Ile Val Met Thr Gln Ser Pro Ser Ser Leu Ala Met Ser Val Gly
```

```
1               5                   10                  15

Gln Lys Val Thr Met Ser Cys Lys Ser Ser Gln Ser Leu Leu Asn Ser
            20                  25                  30

Ser Ser Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Arg Thr Pro Trp Thr Phe Gly Gly Gly Thr Lys Leu Glu Ile
            100                 105                 110

Lys


<210> SEQ ID NO 19
<211> LENGTH: 118
<212> TYPE: PRT
<213> ORGANISM: Artificial Sequence
<220> FEATURE:
<223> OTHER INFORMATION: Synthetic peptide

<400> SEQUENCE: 19

Gln Val Gln Leu Gln Gln Pro Gly Ala Glu Val Val Arg Pro Gly Ala
1               5                   10                  15

Ser Val Lys Leu Ser Cys Lys Ala Ser Gly Tyr Ser Phe Thr Ser Tyr
            20                  25                  30

Trp Ile His Trp Leu Lys Gln Gly Pro His Gln Gly Leu Glu Trp Ile
        35                  40                  45

Gly Arg Ile Asp Pro Asp Asp Ser Glu Thr His Tyr Asn Gln Lys Phe
    50                  55                  60

Lys Asp Lys Ala Leu Leu Thr Val Asp Lys Ser Ser Ser Thr Ala Tyr
65                  70                  75                  80

Met Gln Leu Arg Ser Leu Thr Ser Glu Asp Ser Ala Val Tyr Tyr Cys
                85                  90                  95

Ala Arg Thr Asn Trp Asp Ala Trp Phe Ala Tyr Trp Gly Gln Gly Thr
            100                 105                 110

Leu Val Thr Val Ser Ala
        115


<210> SEQ ID NO 20
<211> LENGTH: 118
<212> TYPE: PRT
<213> ORGANISM: Artificial Sequence
<220> FEATURE:
<223> OTHER INFORMATION: Synthetic peptide

<400> SEQUENCE: 20

Gln Val Gln Leu Gln Gln Pro Gly Ala Glu Val Val Arg Pro Gly Ala
1               5                   10                  15

Ser Val Lys Leu Ser Cys Gln Thr Ser Gly Tyr Ser Phe Thr Ser Tyr
            20                  25                  30

Trp Ile His Trp Leu Lys Gln Gly Pro His Gln Gly Leu Glu Trp Ile
        35                  40                  45

Gly Arg Ile Asp Pro Asp Asp Ser Glu Thr His Tyr Asn Gln Lys Phe
    50                  55                  60

Lys Asp Lys Ala Leu Leu Thr Val Asp Lys Ser Ser Ser Thr Ala Tyr
```

```
65                  70                  75                  80

Met Gln Leu Arg Ser Leu Thr Ser Glu Asp Ser Ala Val Tyr Tyr Cys
                85                  90                  95

Ala Arg Thr Asn Trp Asp Ala Trp Phe Ala Tyr Trp Gly Gln Gly Thr
            100                 105                 110

Leu Val Thr Ala Ser Ala
        115


<210> SEQ ID NO 21
<211> LENGTH: 118
<212> TYPE: PRT
<213> ORGANISM: Artificial Sequence
<220> FEATURE:
<223> OTHER INFORMATION: Synthetic peptide

<400> SEQUENCE: 21

Gln Val Gln Leu Gln Gln Pro Gly Ala Glu Val Val Arg Pro Gly Ala
1               5                   10                  15

Ser Val Lys Leu Ser Cys Lys Ala Ser Gly Tyr Ser Phe Thr Ser Tyr
            20                  25                  30

Trp Ile His Trp Leu Lys Gln Gly Pro His Gln Gly Leu Glu Trp Ile
        35                  40                  45

Gly Arg Leu Asp Pro Asp Asp Ser Glu Thr His Tyr Leu Glu Lys Phe
    50                  55                  60

Gln Gly Lys Glu Leu Leu Thr Val Asp Lys Ser Ser Ser Thr Ala Tyr
65                  70                  75                  80

Met Gln Leu Arg Ser Leu Thr Ser Glu Asp Ser Ala Val Tyr Tyr Cys
                85                  90                  95

Ala Arg Thr Asn Trp Asp Ala Trp Phe Ala Tyr Trp Gly Gln Gly Thr
            100                 105                 110

Leu Val Thr Val Ser Ala
        115


<210> SEQ ID NO 22
<211> LENGTH: 118
<212> TYPE: PRT
<213> ORGANISM: Artificial Sequence
<220> FEATURE:
<223> OTHER INFORMATION: Synthetic peptide

<400> SEQUENCE: 22

Gln Val Gln Leu Gln Gln Pro Gly Ala Glu Val Val Arg Pro Gly Ala
1               5                   10                  15

Ser Val Lys Leu Ser Cys Gln Thr Ser Gly Tyr Ser Phe Thr Ser Tyr
            20                  25                  30

Trp Ile His Trp Leu Lys Gln Gly Pro His Gln Gly Leu Glu Trp Ile
        35                  40                  45

Gly Arg Leu Asp Pro Asp Asp Ser Glu Thr His Tyr Leu Glu Lys Phe
    50                  55                  60

Gln Gly Lys Glu Leu Leu Thr Val Asp Lys Ser Ser Ser Thr Ala Tyr
65                  70                  75                  80

Met Gln Leu Arg Ser Leu Thr Ser Glu Asp Ser Ala Val Tyr Tyr Cys
                85                  90                  95

Ala Arg Thr Asn Trp Asp Ala Trp Phe Ala Tyr Trp Gly Gln Gly Thr
            100                 105                 110

Leu Val Thr Ala Ser Ala
        115
```

-continued

```
<210> SEQ ID NO 23
<211> LENGTH: 8
<212> TYPE: PRT
<213> ORGANISM: Artificial Sequence
<220> FEATURE:
<223> OTHER INFORMATION: Synthetic peptide

<400> SEQUENCE: 23

His His His His His His His His
1               5


<210> SEQ ID NO 24
<211> LENGTH: 7
<212> TYPE: PRT
<213> ORGANISM: Artificial Sequence
<220> FEATURE:
<223> OTHER INFORMATION: Synthetic peptide

<400> SEQUENCE: 24

His His His His His His Lys
1               5


<210> SEQ ID NO 25
<211> LENGTH: 11
<212> TYPE: PRT
<213> ORGANISM: Artificial Sequence
<220> FEATURE:
<223> OTHER INFORMATION: Synthetic peptide

<400> SEQUENCE: 25

His His His His His His Gly Ser Gly Gly Lys
1               5                   10


<210> SEQ ID NO 26
<211> LENGTH: 25
<212> TYPE: PRT
<213> ORGANISM: Artificial Sequence
<220> FEATURE:
<223> OTHER INFORMATION: Synthetic peptide

<400> SEQUENCE: 26

Met Asp Ala Met Lys Arg Gly Leu Cys Cys Val Leu Leu Leu Cys Gly
1               5                   10                  15

Ala Val Phe Val Ser Pro Ser Ala Ser
            20                  25


<210> SEQ ID NO 27
<211> LENGTH: 20
<212> TYPE: PRT
<213> ORGANISM: Artificial Sequence
<220> FEATURE:
<223> OTHER INFORMATION: Synthetic peptide

<400> SEQUENCE: 27

Met Tyr Arg Met Gln Leu Leu Ser Cys Ile Ala Leu Ser Leu Ala Leu
1               5                   10                  15

Val Thr Asn Ser
            20


<210> SEQ ID NO 28
<211> LENGTH: 20
<212> TYPE: PRT
<213> ORGANISM: Artificial Sequence
<220> FEATURE:
<223> OTHER INFORMATION: Synthetic peptide
```

```
<400> SEQUENCE: 28

Met Glu Thr Asp Thr Leu Leu Leu Trp Val Leu Leu Leu Trp Val Pro
1               5                   10                  15

Gly Ser Thr Gly
            20


<210> SEQ ID NO 29
<211> LENGTH: 24
<212> TYPE: PRT
<213> ORGANISM: Artificial Sequence
<220> FEATURE:
<223> OTHER INFORMATION: Synthetic peptide

<400> SEQUENCE: 29

Met Asp Pro Lys Gly Ser Leu Ser Trp Arg Ile Leu Leu Phe Leu Ser
1               5                   10                  15

Leu Ala Phe Glu Leu Ser Tyr Gly
            20


<210> SEQ ID NO 30
<211> LENGTH: 20
<212> TYPE: PRT
<213> ORGANISM: Artificial Sequence
<220> FEATURE:
<223> OTHER INFORMATION: Synthetic peptide

<400> SEQUENCE: 30

Met Glu Thr Asp Thr Leu Leu Leu Trp Val Leu Leu Leu Trp Val Pro
1               5                   10                  15

Gly Ser Thr Gly
            20


<210> SEQ ID NO 31
<211> LENGTH: 17
<212> TYPE: PRT
<213> ORGANISM: Artificial Sequence
<220> FEATURE:
<223> OTHER INFORMATION: Synthetic peptide

<400> SEQUENCE: 31

Lys Ser Ser Gln Ser Leu Leu Asn Ser Ser Ser Gln Lys Asn Tyr Leu
1               5                   10                  15

Ala


<210> SEQ ID NO 32
<211> LENGTH: 7
<212> TYPE: PRT
<213> ORGANISM: Artificial Sequence
<220> FEATURE:
<223> OTHER INFORMATION: Synthetic peptide

<400> SEQUENCE: 32

Phe Ala Ser Thr Arg Glu Ser
1               5


<210> SEQ ID NO 33
<211> LENGTH: 9
<212> TYPE: PRT
<213> ORGANISM: Artificial Sequence
<220> FEATURE:
<223> OTHER INFORMATION: Synthetic peptide

<400> SEQUENCE: 33

Gln Gln His Tyr Arg Thr Pro Trp Thr
```

```
1               5


<210> SEQ ID NO 34
<211> LENGTH: 5
<212> TYPE: PRT
<213> ORGANISM: Artificial Sequence
<220> FEATURE:
<223> OTHER INFORMATION: Synthetic peptide

<400> SEQUENCE: 34

Ser Tyr Trp Ile His
1               5


<210> SEQ ID NO 35
<211> LENGTH: 6
<212> TYPE: PRT
<213> ORGANISM: Artificial Sequence
<220> FEATURE:
<223> OTHER INFORMATION: Synthetic peptide

<400> SEQUENCE: 35

Asp Pro Asp Asp Ser Glu
1               5


<210> SEQ ID NO 36
<211> LENGTH: 9
<212> TYPE: PRT
<213> ORGANISM: Artificial Sequence
<220> FEATURE:
<223> OTHER INFORMATION: Synthetic peptide

<400> SEQUENCE: 36

Thr Asn Trp Asp Ala Trp Phe Ala Tyr
1               5


<210> SEQ ID NO 37
<211> LENGTH: 17
<212> TYPE: PRT
<213> ORGANISM: Artificial Sequence
<220> FEATURE:
<223> OTHER INFORMATION: Synthetic peptide

<400> SEQUENCE: 37

Arg Ile Asp Pro Asp Asp Ser Glu Thr His Tyr Asn Gln Lys Phe Lys
1               5                   10                  15

Asp


<210> SEQ ID NO 38
<211> LENGTH: 17
<212> TYPE: PRT
<213> ORGANISM: Artificial Sequence
<220> FEATURE:
<223> OTHER INFORMATION: Synthetic peptide

<400> SEQUENCE: 38

Arg Leu Asp Pro Asp Asp Ser Glu Thr His Tyr Leu Glu Lys Phe Gln
1               5                   10                  15

Gly
```